US011092532B2

(12) United States Patent
Singh et al.

(10) Patent No.: US 11,092,532 B2
(45) Date of Patent: Aug. 17, 2021

(54) METHOD AND DEVICE FOR LABEL-FREE, HIGH THROUGHPUT HOLOGRAPHIC SCREENING AND ENUMERATION OF TUMOR CELLS IN BLOOD

(71) Applicant: Texas Tech University System, Lubbock, TX (US)

(72) Inventors: Dhananjay Kumar Singh, Lubbock, TX (US); Caroline C. Ahrens, Ambler, PA (US); Wei Li, Lubbock, TX (US); Siva A. Vanapalli, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/621,307

(22) PCT Filed: Jun. 22, 2018

(86) PCT No.: PCT/US2018/038939
§ 371 (c)(1),
(2) Date: Dec. 11, 2019

(87) PCT Pub. No.: WO2018/237239
PCT Pub. Date: Dec. 27, 2018

(65) Prior Publication Data
US 2020/0116617 A1  Apr. 16, 2020

Related U.S. Application Data

(60) Provisional application No. 62/524,006, filed on Jun. 23, 2017.

(51) Int. Cl.
*G01N 15/02* (2006.01)
*G03H 1/04* (2006.01)
(Continued)

(52) U.S. Cl.
CPC ....... *G01N 15/0205* (2013.01); *G03H 1/0443* (2013.01); *G03H 1/0866* (2013.01);
(Continued)

(58) Field of Classification Search
CPC ....... G01N 15/0205; G01N 2015/0233; G01N 2015/1006; G03H 1/0443; G03H 1/0866; G03H 2001/0452
See application file for complete search history.

(56) References Cited

U.S. PATENT DOCUMENTS

| 7,009,700 B2 * | 3/2006 | Dubois | G01N 21/6458 356/317 |
| 2008/0018966 A1 * | 1/2008 | Dubois | G03H 1/0443 359/9 |

(Continued)

OTHER PUBLICATIONS

Aceto, N. et al. Circulating tumor cell clusters are oligoclonal precursors of breast cancer metastasis. Cell 158, 1110-1122, (2014).
(Continued)

*Primary Examiner* — Michael A Lyons
(74) *Attorney, Agent, or Firm* — Edwin S. Flores; Daniel J. Chalker; Chalker Flores, LLP

(57) ABSTRACT

The present invention includes method and device for label-free holographic screening and enumeration of tumor cells in bulk flow comprising: a laser source, a micro-objective, a pinhole device and a collimating lens, a mirror, a sample chamber with a sample flow inlet on a first side of the sample chamber and a sample flow outlet connected by a micro-channel, and a detector, wherein the collimated laser beam passes through microchannel and interacts with cells in the sample to generate a respective hologram at the detector, wherein a processor calculates a numerical reconstruction from the respective hologram and generates a focused image of the numerous cells using the numerical reconstruction,
(Continued)

wherein the numerous cells are enumerated by looking at a size, a maximum intensity and a mean intensity of the focused image.

20 Claims, 14 Drawing Sheets

(51) Int. Cl.
  *G03H 1/08* (2006.01)
  *G01N 33/50* (2006.01)
  *G01N 15/10* (2006.01)
(52) U.S. Cl.
  CPC .. *G01N 33/5011* (2013.01); *G01N 2015/0233* (2013.01); *G01N 2015/1006* (2013.01); *G03H 2001/0447* (2013.01); *G03H 2001/0452* (2013.01)

(56) References Cited

U.S. PATENT DOCUMENTS

| | | | |
|---|---|---|---|
| 2013/0148182 A1* | 6/2013 | Yu | G03H 1/0443 359/22 |
| 2014/0349336 A1 | 11/2014 | Magniette | |
| 2015/0056607 A1 | 2/2015 | Jooris et al. | |
| 2016/0131882 A1 | 5/2016 | Wallace et al. | |
| 2017/0061619 A1 | 3/2017 | Lagae et al. | |
| 2018/0365810 A1* | 12/2018 | Khare | G06T 5/003 |

OTHER PUBLICATIONS

Bagnall, J. S. et al. Deformability-based cell selection with downstream immunofluorescence analysis. Integrative Biology 8, 654-664 (2016).
Che, J. et al. Classification of large circulating tumor cells isolated with ultra-high throughput microfluidic Vortex technology. Oncotarget 7, 12748-12760 (2016).
Choi, W. et al. Tomographic phase microscopy. Nature methods 4, 717 (2007).
Choi, Y et al. Three-dimensional volumetric measurement of red blood cell motion using digital holographic microscopy. Appl. Opt. 48, 2983-2990 (2009).
Duffy, D. C. et al. Rapid prototyping of microfluidic systems in poly (dimethylsiloxane). Anal. Chem. 70, 4974-4984 (1998).
Fang, Y. Label-free drug discovery. Front. Pharmacol. 5, 52, (2014).
Ferreira, M. M. et al. Circulating tumor cell technologies. Mol Oncol 10, 374-394, (2016).
Harouaka, R. A. et al. Circulating tumor cell enrichment based on physical properties. Journal of laboratory automation 18, 455-468 (2013).
Hou, H. W. et al. Isolation and retrieval of circulating tumor cells using centrifugal forces. Scientific Reports 3, 1259, http://www.nature.com/articles/srep01259#supplementary-information (2013).
Huang, L. R. et al. Continuous particle separation through deterministic lateral displacement. Science 304, 987-990 (2004).
Kim, M. K. Principles and techniques of digital holographic microscopy. J. of Photonics for Energy, 018005, (2010).
Li, P. et al. Acoustic separation of circulating tumor cells. Proceedings of the National Academy of Sciences 112, 4970-4975 (2015).
Liang, X. et al. Determining refractive index of single living cell using an integrated microchip. Sensors and Actuators A: Physical 133, 349-354 (2007).
Liu, P. et al. Cell refractive index for cell biology and disease diagnosis: past, present and future. Lab on a Chip 16, 634-644 (2016).
Maheswaran, S. et al. Circulating tumor cells: a window into cancer biology and metastasis. Curr Opin Genet Dev 20, 96-99, (2010).
Maheswaran, S. et al. Detection of mutations in EGFR in circulating lung-cancer cells. New England Journal of Medicine 359, 366-377 (2008).
Maltsev, V. P. et al. Optics of white blood cells: optical models, simulations, and experiments. Exp Tech 4 (2011).
Mitra, R. et al. Detection of lipid-rich prostate circulating tumour cells with coherent anti-Stokes Raman scattering microscopy. BMC Cancer 12, 540, (2012).
Moon, H. S. et al. Continual collection and re-separation of circulating tumor cells from blood using multi-stage multi-orifice flow fractionation. Biomicrofluidics 7, 14105, (2013).
International Search Report and Written Opinion, [ISA/AU] PCT/US2018/038939, dated Sep. 26, 2018.
Mullaney, P. et al. Cell sizing: a light scattering photometer for rapid volume determination. Rev. Sci. Instrum. 40, 1029-1032 (1969).
Ozkumur, E. et al. Inertial focusing for tumor antigen-dependent and-independent sorting of rare circulating tumor cells. Science translational medicine 5, 179ra147-179ra147 (2013).
Pantel, K. et al. The biology of circulating tumor cells. Oncogene 35, 1216-1224, (2016).
Reategui, E. et al. Tunable nanostructured coating for the capture and selective release of viable circulating tumor cells. Adv Mater 27, 1593-1599 (2015).
Shim, S. et al. Antibody-independent isolation of circulating tumor cells by continuous-flow dielectrophoresis. Biomicrofluidics 7, 11807 (2013).
Singh, D. K, et al., "Label-free, high-throughput holographic screening and enumeration of tumor cells in blood", Lab on a Chip 17, 2920-2932, (2017), published online Jul. 10, 2017.
Singh, D. K. et al. Automatic threshold technique for holographic particle field characterization. Applied Optics 51, 3874-3887 (2012).
Singh, D. K. Improved digital holographic reconstruction algorithm for depth error reduction and elimination of out-of-focus particles. Opt Express 18, 2426-2448, (2010).
Singh, D. K. et al. Three-dimensional investigation of liquid slug Taylor flow inside a micro-capillary using holographic velocimetry. Experiments in Fluids 56, 1-15, (2015).
Singh, D. K. et al. Label-free fingerprinting of tumor cells in bulk flow using inline digital holographic microscopy. Biomed. Opt. Express 8, 536-554, (2017).
Van der Toom, E. E. et al. Technical challenges in the isolation and analysis of circulating tumor cells. Oncotarget 7, 62754-62766 (2016).
Warkiani, M. E. et al. Slanted spiral microfluidics for the ultra-fast, label-free isolation of circulating tumor cells. Lab on a Chip 14, 128-137 (2014).
X. Liang, et al. Determining refractive index of single living cell using an integrated microchip. Sensors and Actuators A: Physical 133, 349-354 (2007).
Yu, M. et al. Circulating tumor cells: approaches to isolation and characterization. The Journal of cell biology 192, 373-382, (2011).
Zhang, J. et al. Fundamentals and applications of inertial microfluidics: a review. Lab Chip 16, 10-34, (2016).
Zhao, Y. et al. Method for the accurate preparation of cell-spiking standards. Analytical chemistry 81, 1285-1290 (2008).

\* cited by examiner

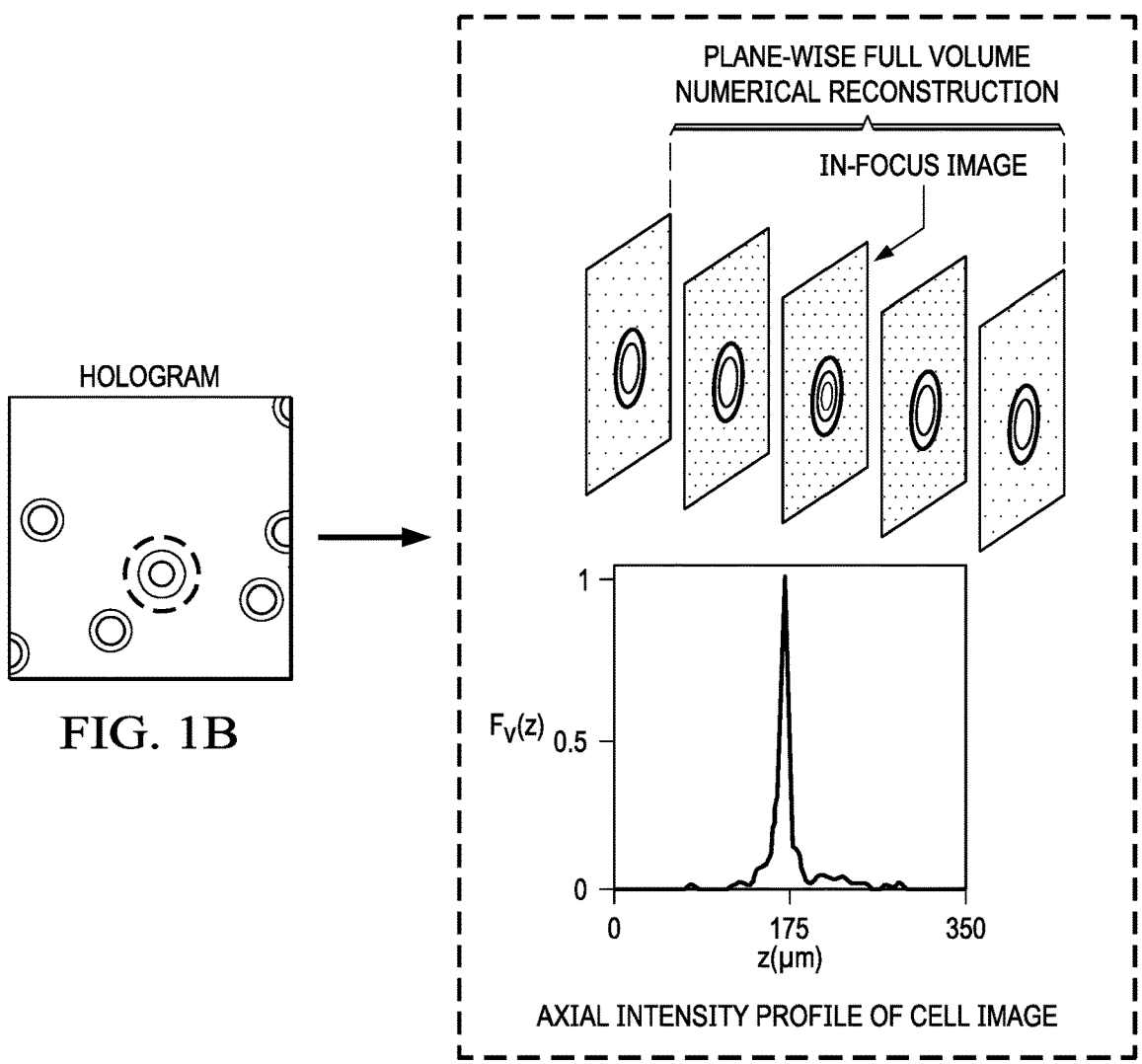
FIG. 1B
FIG. 1C
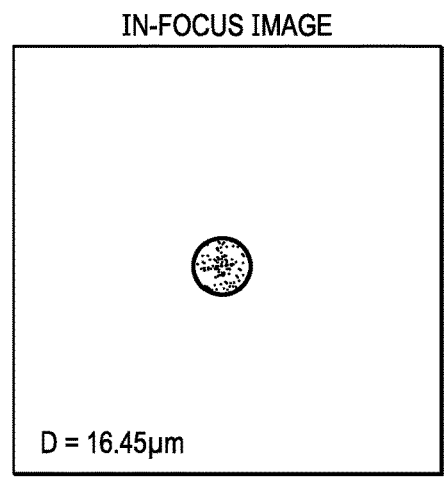
FIG. 1D

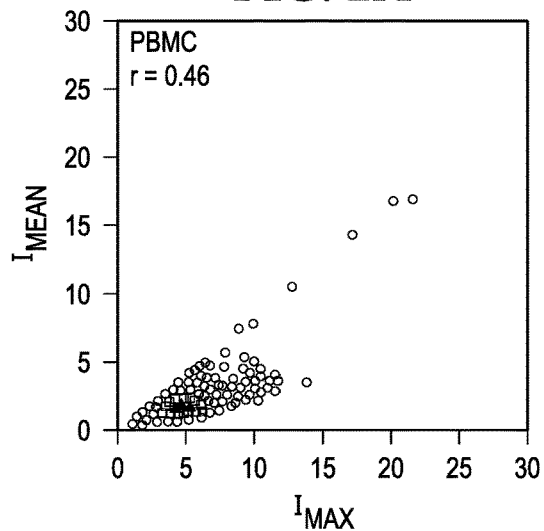
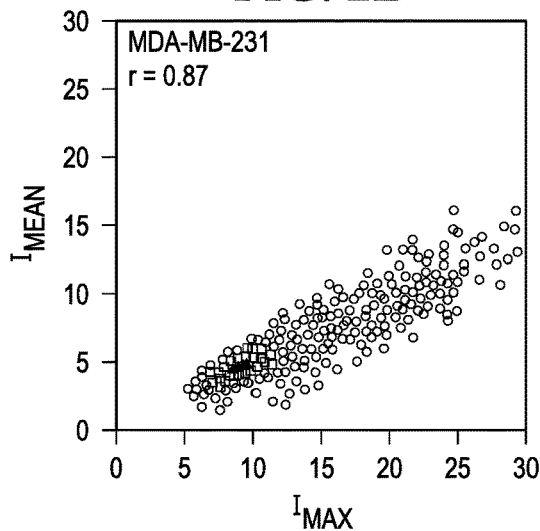
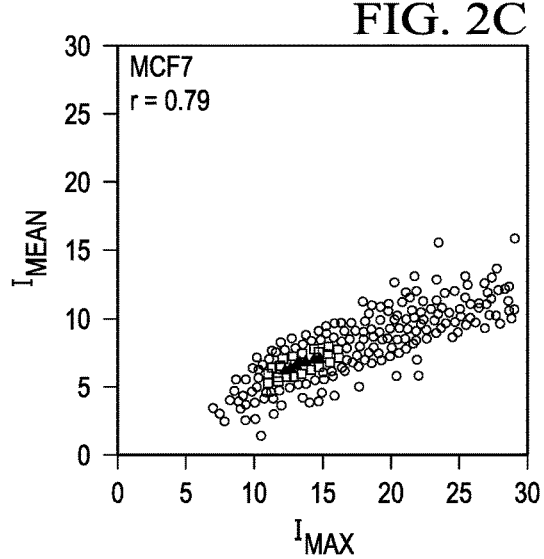
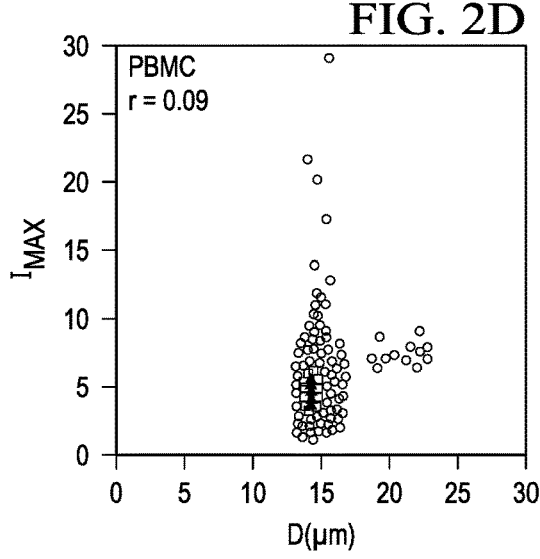
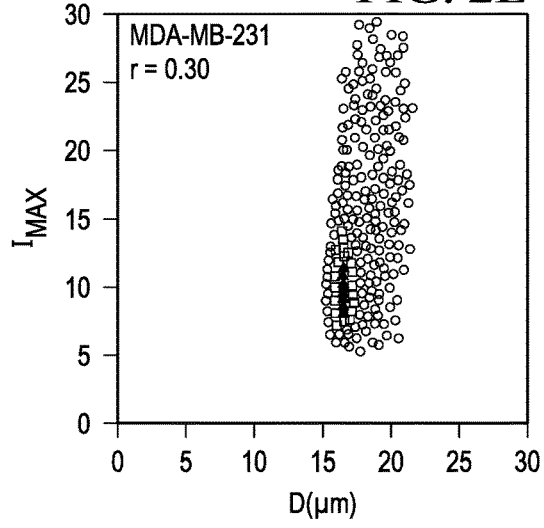
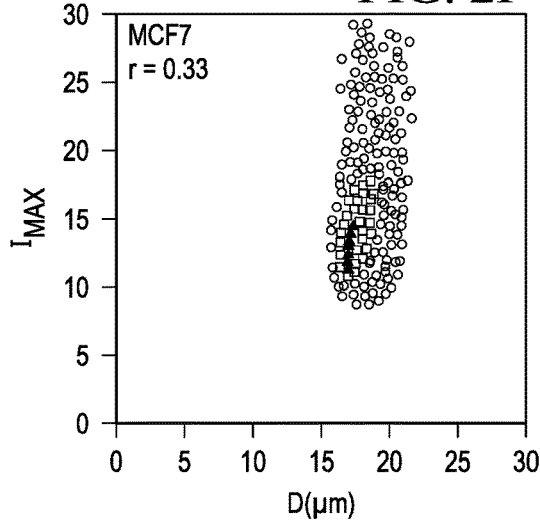

FIG. 7C
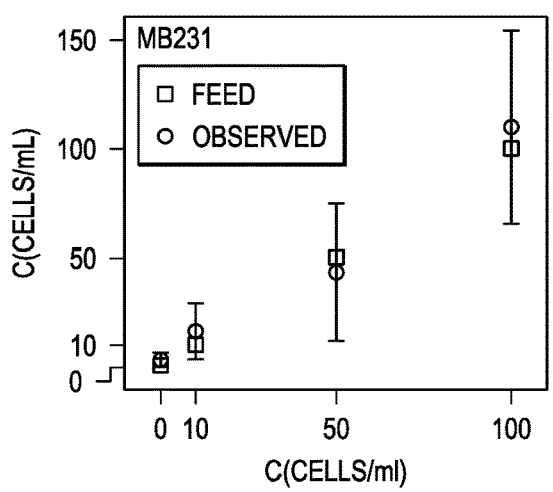
FIG. 7D
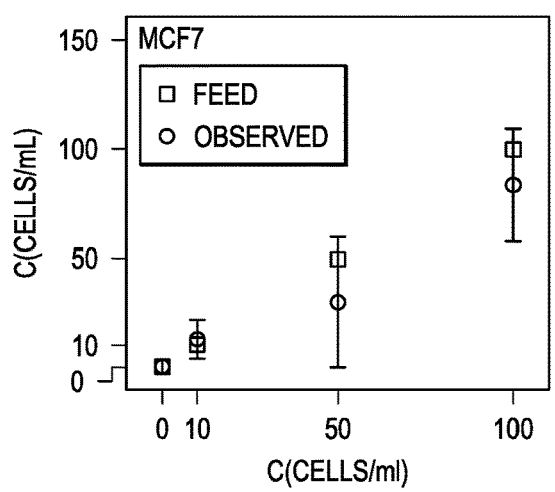
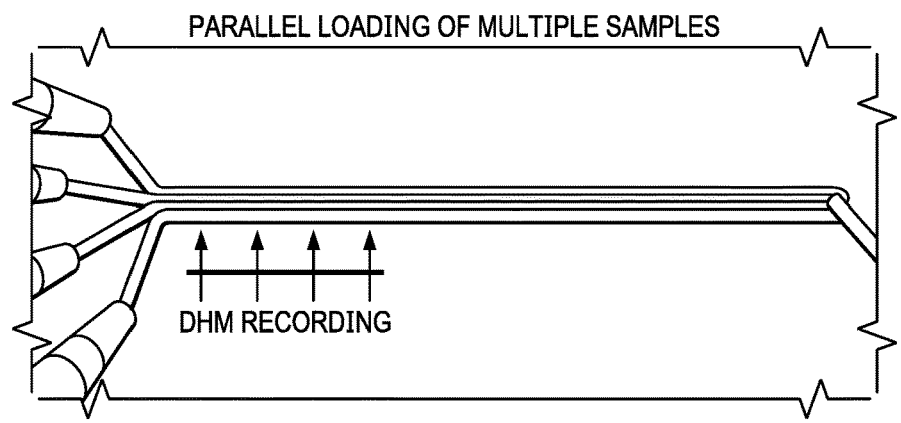
FIG. 8A
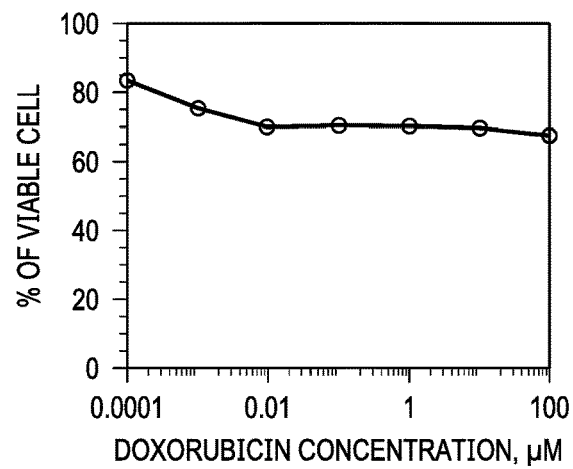
FIG. 8B

METHOD AND DEVICE FOR LABEL-FREE, HIGH THROUGHPUT HOLOGRAPHIC SCREENING AND ENUMERATION OF TUMOR CELLS IN BLOOD

CROSS-REFERENCE TO RELATED APPLICATIONS

This application is the National Stage of International Application No. PCT/US2018/038939, filed on Jun. 22, 2018, which claims priority to U.S. Patent Appl. Ser. No. 62/524,006, filed Jun. 23, 2017, the content of each of which is incorporated by reference herein.

TECHNICAL FIELD OF THE INVENTION

The present invention relates generally to methods and compositions used in connection with holographic screening, identifying, classifying and enumeration of tumor cells in blood.

BACKGROUND OF THE INVENTION

Without limiting the scope of the invention, its background is described in connection with cancer treatments and more specifically to method and device for holographic screening and enumeration of tumor cells in blood.

Circulating tumor cells (CTCs) are cells that have entered the peripheral blood of cancer patients after having left primary or metastatic tumors. Identifying the presence and assessing the characteristics of these CTCs through liquid biopsies has shown great promise for improving cancer patient care by enabling early cancer detection through point-of-care diagnostics, more accurate patient prognosis, and the better direction longitudinal treatments options.

Current methods of selective CTC identification require coupled labeling with fluorescent markers and antibodies. Although this antibody method has proven successful, it requires the fixation and permeabilization of cells for analysis, which eliminates future phenotypic assays and further downstream processing. Ideally, identification techniques should permit label-free marking, high-throughput potential, and platform flexibility.

U.S. Patent Application Publication No. 2014/0349336, entitled, "Sample vial for digital holographic analysis of a liquid cell sample," discloses a sample vial for receiving a liquid cell sample, to be used in conjunction with a digital holographic microscope (DHM), said sample vial comprises at least two compartments in fluid connection with one another, said compartments comprising at least one pair of screening surfaces, said screening surfaces are essentially flat; and characterized in that the distance between the pair of screening surfaces of the second compartment is smaller than the distance between the pair of screening surfaces of the first compartment.

SUMMARY OF THE INVENTION

In one embodiment, the present invention includes a digital holographic microscope to enumerate cells in bulk flow comprising: a laser source for providing a laser beam; a micro-objective, a pinhole device and a collimating lens in optical communication with the collimated laser beam; a mirror in optical communication with the collimated laser beam; a sample chamber in optical communication with the mirror, wherein the sample chamber comprises a sample flow inlet on a first side of the sample chamber connected to a sample flow outlet on a second side of the sample chamber by a microchannel, wherein a sample comprising numerous cells is transported at a bulk flow rate through the microchannel from the sample flow inlet to the sample flow outlet; a detector in optical communication with the microchannel, wherein the collimated laser beam passes through microchannel and interacts with the numerous cells to generate a respective hologram at the detector; wherein the detector obtains a numerical reconstruction from the respective hologram; and wherein the detector obtains a focused image of the numerous cells using the numerical reconstruction. In one aspect, the numerous cells are enumerated by looking at a size, a maximum intensity and a mean intensity of the focused image. In another aspect, the sample chamber comprises more than two parallel paths to accommodate more than two parallel samples. In another aspect, the device further comprises a loading stage having more than two parallel sample paths in parallel communication with more than two parallel paths in parallel communication with more than two parallel microchannels to accommodate more than two parallel samples. In another aspect, the detector or a processor finger-prints the numerous cells based on wherein the numerous cells are enumerated by looking at a size, a maximum intensity and a mean intensity of the focused image. In another aspect, the hologram is recorded and transferred to computer and a three-dimensional numerical reconstruction of the focused image of sample in the 3D volume is generated using the hologram and a z-location of the focused image formed by the profile of the gradient of intensity along a z-direction. In another aspect, the detector records an in-focus image of the sample; the detector records the interference pattern (hologram) between light scattered from the sample and the un-scattered light or both.

In one embodiment, the present invention includes a digital holographic microscope comprising: a laser source for providing a laser beam; a micro-objective, a pinhole device and a collimating lens in optical communication with the collimated laser beam; a mirror in optical communication with the collimated laser beam; a sample chamber in optical communication with the mirror, wherein the sample chamber comprises a sample flow inlet on a first side of the sample chamber connected to a sample flow outlet on a second side of the sample chamber by a microchannel, wherein a sample is transported at a flow rate through the microchannel from the sample flow inlet to the sample flow outlet; and a detector in optical communication with the microchannel, wherein the collimated laser beam passes through microchannel and interacts with the sample to generate a hologram at the detector. In one aspect, the numerous cells are enumerated by looking at a size, a maximum intensity and a mean intensity of the focused image. In another aspect, the sample chamber comprises more than two parallel paths to accommodate more than two parallel samples. In another aspect, the microscope further comprises a loading stage having more than two parallel sample paths in parallel communication with more than two parallel paths in parallel communication with more than two parallel microchannels to accommodate more than two parallel samples. In another aspect, the detector or a processor finger-prints the numerous cells based on wherein the numerous cells are enumerated by looking at a size, a maximum intensity and a mean intensity of the focused image. In another aspect, the hologram is recorded and transferred to computer and a three-dimensional numerical reconstruction of the focused image of sample in the 3D volume is generated using the hologram and a z-location of the focused image formed by the profile of the gradient of intensity along a z-direction. In another aspect, the detector records an in-focus image of the sample; the detector records the interference pattern (hologram) between light scattered from the sample and the un-scattered light or both.

In one embodiment, the present invention includes a method of quantifying tumor cells using a digital holographic microscope comprising the steps of: providing a digital holographic microscope comprising a laser source for providing a laser beam, the microscope comprising: a microobjective, a pinhole device and a collimating lens in optical communication with the collimated laser beam; a mirror in optical communication with the collimated laser beam; a sample chamber in optical communication with the mirror, wherein the sample chamber comprises a sample flow inlet on a first side of the sample chamber connected to a sample flow outlet on a second side of the sample chamber by a microchannel, wherein a sample is transported at a flow rate through the microchannel from the sample flow inlet to the sample flow outlet; and a detector in optical communication with the microchannel, wherein the collimated laser beam passes through microchannel and interacts with the sample to generate a hologram at the detector; passing a sample through the microchannel; contacting the sample with the collimated laser beam to form a sample image; recording one or more sample characteristics; providing a catalog of reference images defining one or more reference characteristics; comparing the one or more sample characteristics to the one or more reference characteristics to generate an analyzed sample; and using the analyzed sample to quantifying the sample content. In one aspect, the method further comprises enumerating the numerous cells by analyzing at a size, a maximum intensity and a mean intensity of the focused image. In another aspect, the sample chamber comprises more than two parallel paths to accommodate more than two parallel samples. In another aspect, the method further comprises a loading stage having more than two parallel sample paths in parallel communication with more than two parallel paths in parallel communication with more than two parallel microchannels to accommodate more than two parallel samples. In another aspect, the method further comprises fingerprinting the numerous cells based on wherein the numerous cells are enumerated by looking at a size, a maximum intensity and a mean intensity of the focused image. In another aspect, the method further comprises recording the hologram is recorded to computer and a three-dimensional numerical reconstruction of the focused image of sample in the 3D volume is generated using the hologram and a z-location of the focused image formed by the profile of the gradient of intensity along a z-direction. In another aspect, the method further comprises transferring the hologram to computer and a three-dimensional numerical reconstruction of the focused image of sample in the 3D volume is generated using the hologram and a z-location of the focused image formed by the profile of the gradient of intensity along a z-direction. In another aspect, the method further comprises recording and transferring the hologram to computer and a three-dimensional numerical reconstruction of the focused image of sample in the 3D volume is generated using the hologram and a z-location of the focused image formed by the profile of the gradient of intensity along a z-direction. In another aspect, the detector records an in-focus image of the sample; the detector records the interference pattern (hologram) between light scattered from the sample and the un-scattered light or both.

DESCRIPTION OF THE DRAWINGS

For a more complete understanding of the features and advantages of the present invention, reference is now made to the detailed description of the invention along with the accompanying FIGS. and in which:

FIGS. 1A-1F show principle of inline digital holography microscopy (DHM) for characterizing cells in flow. FIG. 1A shows the arrangement of inline-DHM for recording holograms of cells in bulk flow and the experimental parameters used in this study. Here MO: Microscope objective, PH: Pinhole, CL: Collimating lens. FIG. 1B shows the hologram cropped from the original hologram of MCF7 cells. FIG. 1C shows the three-dimensional numerical reconstruction to generate the focused image of cells in the 3D volume, a 2D in-focus image corresponding to the hologram pattern encircled in (FIG. 1B) and the z-location of the focused image shown by the profile of the gradient of intensity along the z-direction. FIG. 1D shows a representative in-focus image of a single MCF7 cell. FIG. 1E shows the intensity profile along a line passing through the center of the in-focus image on the xy-plane. FIG. 1F is a heat map of (FIG. 1D). The maximum intensity ($I_{max}$) corresponding to the single brightest pixel is indicated with an arrow and the perimeter of the region of mean intensity ($I_{mean}$) corresponding to 6×6 $\mu m^2$ is indicated by a dashed area.

FIGS. 2A-2I are images of binary correlations between the three metrics of size (D), maximum ($I_{max}$) and mean ($I_{mean}$) intensity.

FIGS. 7A-7D are graphs of identification and enumeration of tumor cells spiked in lysed whole blood.

FIGS. 8A and 8B are images of parallelize DHM cytometry for drug response analysis.

DESCRIPTION OF THE INVENTION

Figure 1A:
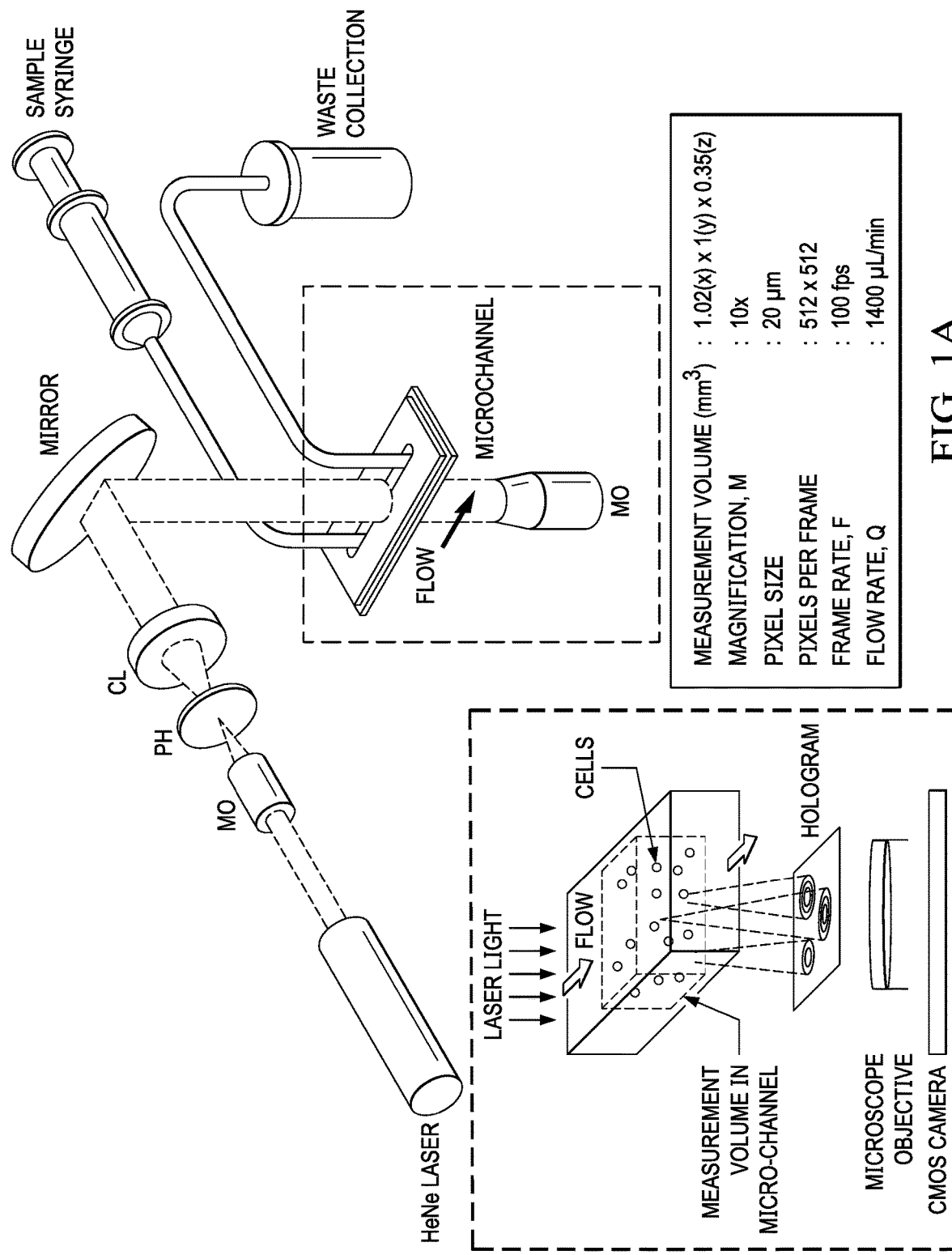

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "DHM" refers to a Digital Holography Microscopy. Digital Holographic Microscopy (DHM) is a non-invasive, label-free, 3-dimensional imaging tool which makes it possible to image all micron-sized objects like biological cells across entire depth of a sample volume using single camera and single illuminating source. In DHM imaging, the interference pattern (hologram) between light scattered from cells in the sample volume and the incident laser beam is recorded on a camera. The light scattered from a cell is its unique signature. It depends on the refractive index, intracellular properties, size and morphology of the cell. Thus, the numerical reconstruction of hologram provides the fingerprint of the cell. Any change in the size and refractive index of cells is manifested in the intensity distribution of focused images obtained using DHM.

The present invention provides an inline digital holographic microscopy as a label-free technique for detecting tumor cells in blood. The optimized DHM platform fingerprints every cell flowing through a microchannel at 10,000 cells per second, based on three features—size, maximum intensity and mean intensity. To identify tumor cells in a background of blood cells, The inventors developed robust gating criteria using machine-learning approaches. The inventors established classifiers from the features extracted from 100,000-cell training sets consisting of red blood cells, peripheral blood mononuclear cells and tumor cell lines. The optimized classifier was then applied to targeted features of a single cell in a mixed cell population to make quantitative cell-type predictions. The inventors tested the classification system with tumor cells spiked at different levels into a background of lysed blood that contained predominantly peripheral blood mononuclear cells. Results show that the holographic screening method can readily detect as few as 10 tumor cells/mL, and can identify tumor cells at a false positive rate of at most 0.001%. This purely optical approach obviates the need for antibody labeling and allows large volumes of sample to be quickly processed. Moreover, the in-line DHM approach can be combined with existing circulation tumor cell enrichment strategies, making it a promising tool for label-free analysis of liquid-biopsy samples.

Circulating tumor cells (CTCs) have been identified in the blood of cancer patients as those cells that have left primary or even metastatic tumors and entered into peripheral blood. As part of so-called liquid biopsies[1], identifying the presence and assessing the character of CTCs has shown great utility for improving patient care including enabling early cancer detection, determining patient prognosis, and directing longitudinal treatments[2-4]. Clinical success has motivated the development of a variety of technologies to identify, isolate, and characterize the extremely rare subpopulation of CTCs in patient blood (approximately 1-10 CTCs in 1 billion blood cells).[5] Established methods for CTC characterization largely rely on differences in biochemical and physical properties between CTCs and blood cells to recover a population enriched in CTCs 5. Biochemical techniques typically involve the selective arrest of tumor cells through surface binding of proteins preferentially expressed on the tumor cell surface 5. In physical separation approaches, the larger average size of tumor cells compared to blood cells and their distinct viscoelastic properties[6] allow for CTC isolation using various filtration and inertial separation techniques[3]. Following CTC enrichment, additional characterization, most often via immunofluorescence, is used to identify CTCs among contaminating blood cells[5]. This subsequent processing is necessary to allow accurate CTC enumeration and is useful in identifying and isolating a pure CTC population appropriate for genomic, proteomic, or phenotypic assays[5,7]. As the field of CTC isolation and characterization continues to develop, traditional techniques involving selective enrichment followed by label-based CTC identification have become increasingly limiting. Labeling molecules including antibodies used in immunofluorescent staining must be validated for each population with varied resolution dependent on label selection[8]. Further, while select immunofluorescence detection strategies preserve cell viability,[9] fixation and permeabilization remain standard for antibody-based characterization[7,10]. This destructive processing improves cell retention and stability but eliminates the potential for subsequent phenotypic assays. A more optimal characterization technique would be label free, high-throughput and platform flexible[11]. Most importantly, the approach should be non-destructive, allowing the recovery of both viable tumor cells and even tumor cell clusters[12] for further downstream processing. Such a technique might be integrated into existing CTC isolation strategies or serve as a stand-alone method for CTC detection. Several cell characterization technologies have begun to meet these demands for alternative detection. Most common are inertial methods introduced above in which cells are flowed through highly structured microfluidic chips. Differences in size and deformability between tumor cells and blood cells in flow are used to isolate a cell population enriched in CTCs[13]. However, the overlapping physical properties of the cell types limit recovered cell purity, requiring secondary processing[7,10,14]. The present invention identified CTCs in a single metastatic prostate cancer patient based on cell passage time through a constriction and buoyant mass, however this developing approach has limited throughput (~45 μL/h) and imperfect resolution, detecting spiked cells with a true positive rate of less than 0.7 even with stringent gating[15]. Label-free Raman spectroscopy is an optical technique used to differentiate tumor cells from blood cells based on inherent differences in amino acid and lipid compositions in the two cell populations[16], but the label-free technique has limited throughput with demonstrated characterization of less than 500 cells. Other strategies include so-called dielectrophoresis[17] and acoustophoresis,[18] in which electrical and acoustic forces, respectively, have been integrated into microfluidic devices to direct label-free cell separation. These separations are broadly based on a variety of factors including difference in cell size, density, mass, compressibility, shape, and, in the case of dielectrophoresis, electrical properties, but both methods have limited throughput and purity.

Here, the inventors introduce inline digital holography microscopy (inline-DHM) as an optical, label-free technique for tumor cell identification in mixed samples. In DHM, the interference pattern (hologram) in an image contains information not only about the cells that are in focus but also cells that are out-of-focus i.e. from entire volume. Using diffraction theories, numerical reconstruction is pursued to obtain the in-focus image of every cell in the 3D volume. Because mechanical scanning across sample depth is not needed, holograms can be acquired at much faster rates using high-speed cameras, making the method suitable for large-scale single cell phenotyping. The inventors recently optimized the DHM set up and demonstrated the label free fingerprinting of thousands of tumor cells in bulk flow[19].

Building on these capabilities of DHM, the main challenge the inventors seek to address here is how to identify rare cancer cells that are present in a mixed population of other cells. The inventors exploit both the size and optical characteristics of different cell types to enumerate tumor cells spiked in blood. Training sets of red blood cells (RBCs), peripheral blood mononuclear cells (PBMCs) and tumor cell lines are used to establish rigorous single- and multidimensional gating strategies for cell identification with a focus on limiting false positives. These optimized selection criteria are applied to identify tumor cells spiked into lysed whole blood based on key physical differences between the blood and tumor cell types.

Figure 1E:
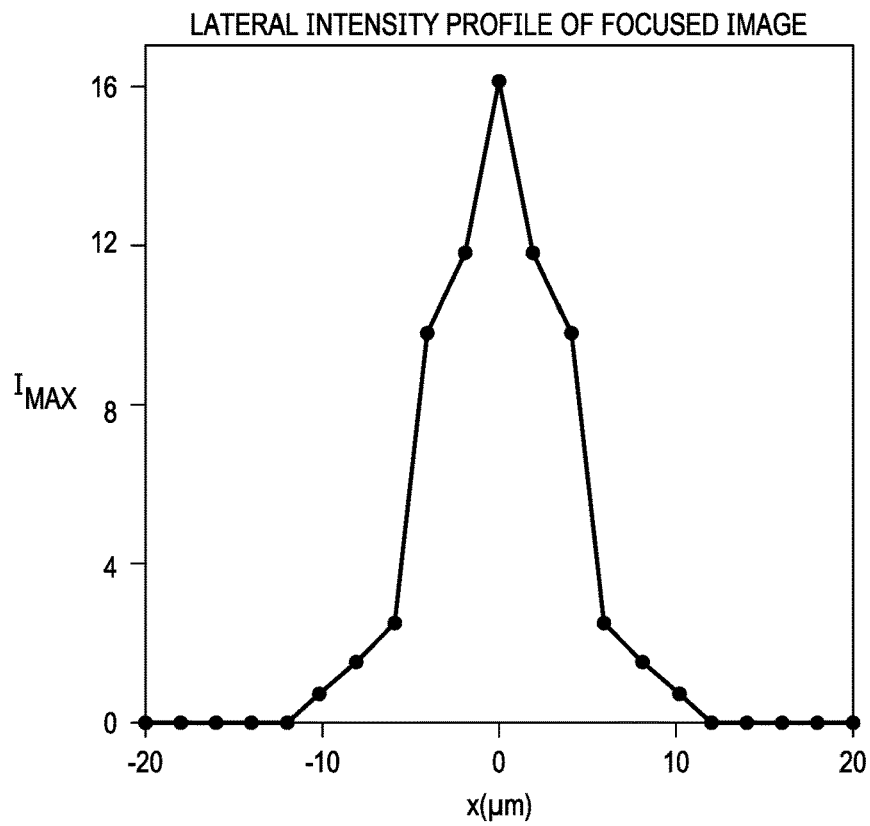
Figure 1F:
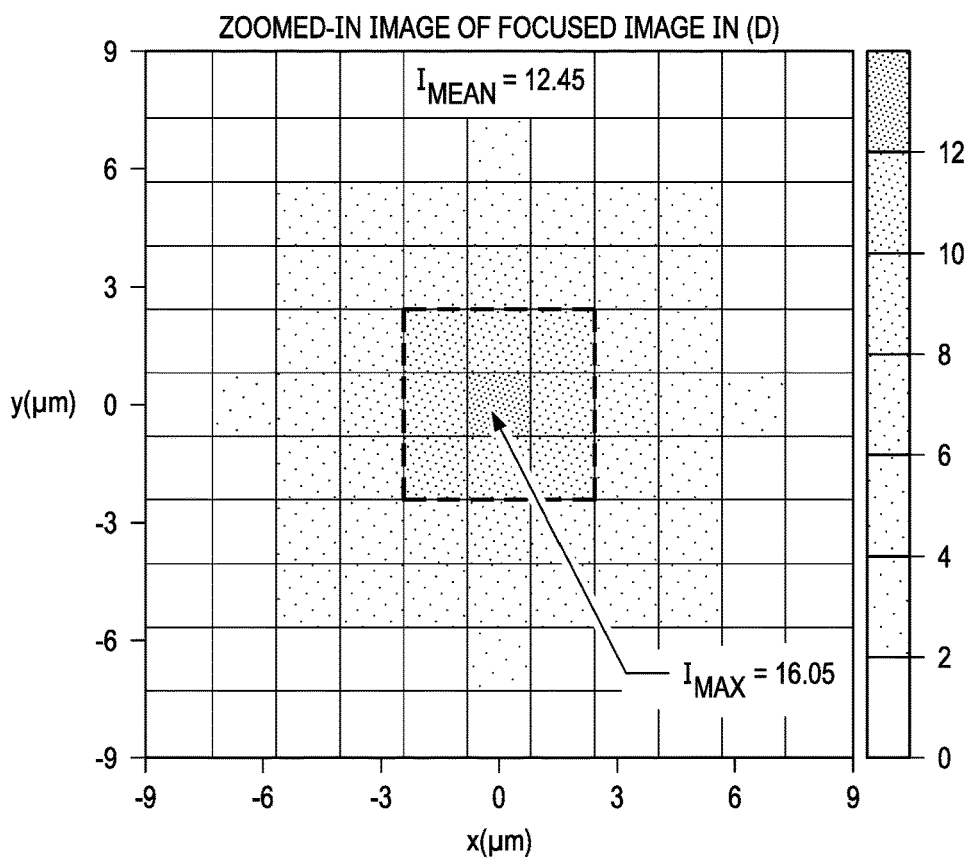

FIGS. 1A-1F illustrate the principle of inline digital holography microscopy (DHM) for characterizing cells in flow. FIG. 1A shows the experimental arrangement of inline-DHM for recording holograms of cells in bulk flow and the experimental parameters used in this study. Here MO: Microscope objective, PH: Pinhole, CL: Collimating lens. FIG. 1B shows the hologram cropped from the original hologram of MCF7 cells. FIG. 1C shows the three-dimensional numerical reconstruction to generate the focused image of cells in the 3D volume, a 2D in-focus image corresponding to the hologram pattern encircled in (FIG. 1B) and the z-location of the focused image shown by the profile of the gradient of intensity along the z-direction. FIG. 1D shows a representative in-focus image of a single MCF7 cell. FIG. 1E shows the intensity profile along a line passing through the center of the in-focus image on the xy-plane. FIG. 1F is a heat map of (FIG. 1D). The maximum intensity ($I_{max}$) corresponding to the single brightest pixel is indicated with an arrow and the perimeter of the region of mean intensity ($I_{mean}$) corresponding to 6×6 µm$^2$ is indicated by a dashed area.

Basic principle of inline-DHM for characterizing cells in bulk flow. This section presents the basic principles of recording and reconstruction of optical signatures from cells in bulk flow using inline-DHM. FIG. 1A shows the experimental arrangement of inline-DHM. In brief, the sample volume containing flowing cells in a transparent microchannel is illuminated by a collimated beam of laser light. The forward scattered light from cells and un-scattered light interfere and generate a 2D hologram. The interference pattern is magnified by a microscope objective and imaged onto a CCD sensor. FIG. 1B shows a portion of hologram from MCF7 cells flowing in a rectangular PDMS channel.

The numerical reconstruction of the 2D hologram provides the focused images of cells in the full volume. The size and intensity distributions of the focused image can be obtained numerically. The intensity distribution across the focused image manifests the recorded intensity in the form of a hologram. FIG. 1C shows the plane-wise 3D numerical reconstruction carried out in the full sample volume from the 2D digital hologram shown in FIG. 1B. The reconstruction is performed using the angular spectrum method[20-22] where the gradient of intensity[23] of the cell image along z-direction inside the reconstruction volume indicates the plane of best focus of each cell image. The focused image provides the size and intensity distributions. FIG. 1D shows a representative focused image of a single MCF7 cell and FIG. 1E shows the intensity distribution along the line passing through the center of this image. Detailed reconstruction methodology for characterization of particles[24-26] and of cells is described in the previous work[19]. From the focused image the inventors extract three metrics quantifying the cell size and image intensity. As established in the previous work the equivalent circular diameter (D) of the focused image provides a characteristic metric of cell size. As shown in FIG. 1E, two optical metrics $I_{max}$ and $I_{mean}$ further characterize the cell. Here $I_{max}$ is the intensity of the single brightest pixel (2×2 µm$^2$) within a given cell image, and $I_{mean}$ is the average intensity of the 6×6 µm$^2$ region centered around the most intense pixel.

Label-free, high throughput tumor cell enumeration via inline-DHM relies on precise and accurate characterization of the size and optical properties of cells flowing through the chosen geometry. In this section, the inventors characterize beads of known character flowing through a straight rectangular PDMS channel to systematically establish the accuracy and precision of inline-DHM recorded particle size and optical properties. The inventors chose cell-sized beads having varied refractive indexes to establish three distinct metrics, size (D) and maximum ($I_{max}$) and mean ($I_{mean}$) intensities. Finally, the inventors explore the interdependence of these metrics and suggest their additive utility when characterizing both beads and cells. The inventors first quantify bead diameters, confirming the accuracy and precision of high throughput inline-DHM based imaging of particles throughout the depth of a 350 µm rectangular PDMS channel. The manufacturer and DHM data for cell-sized (nominal 8 and 15 µm) polystyrene (PS) and silica (SILICA) beads were compared. Bead average diameters and variances of all four bead types, as quantified by DHM, closely match those reported by the manufacturer (Table 1). Further the inventors observed no statistically significant positional variance in diameter measurements (data not shown) confirming the previously published work which established both accurate and precise particle size measurements throughout this depth of flow[19].

TABLE 1

The distribution [µ ± CV(%)] of diameter (D), maximum intensity ($I_{max}$), and mean intensity ($I_{mean}$), of polystyrene (PS) and silica (SILICA) beads obtained from inline-DHM. The data was generated from atleast 100,000 particles for each bead type.

| Bead Type | Manufacturer Data | | DHM Data | | |
|---|---|---|---|---|---|
| | D | RI | D | $I_{max}$ | $I_{mean}$ |
| Polystyrene | 8.23 µm ± 6% | 1.59 | 8.32 µm ± 9% | 0.86 ± 25% | 0.37 ± 20% |
| SILICA | 8.32 µm ± 6% | 1.4 | 8.39 µm ± 9% | 1.68 ± 25% | 0.47 ± 20% |
| Polystyrene | 15.13 µm ± 6% | 1.59 | 15.14 µm ± 3% | 2.41 ± 32% | 0.49 ± 24% |
| SILICA | 15.14 µm ± 3% | 1.4 | 15.32 µm ± 4% | 4.68 ± 32% | 0.91 ± 24% |

The inventors next introduce the two optical metrics, $I_{max}$ and $I_{mean}$ and explore their dependencies on both bead size and inherent optical properties. In the present study, the holograms are generated using the forward scattered light from the beads/cells. A study characterizing beads suspended in water found that S=0.15 D$^3$ and 0.29 D$^{3.3}$ for beads having refractive indices 1.59 and 1.40 respectively, where S is the forward scattering intensity collected within a 2° angle and D is the diameter of the beads[27]. Thus, the forward scattered light predominantly depends on the size of the beads and increases with the increase in bead diameter and decreases with the increase in the bead refractive index[28]. These previous findings support that the forward scattered light contains the information of size and refractive index of a particle but, predominantly, depends on the particle size.

Experimentally observed values of $I_{max}$ and $I_{mean}$ for the four bead populations generally follow expected trends (Table 1). Considering first $I_{max}$, the average recorded intensities for the four bead types range from 0.86 to 4.68 (Table 1). The inventors find $I_{max}$ is higher for beads having the same diameter but lower refractive index, and is higher for larger beads with the same refractive index (Table 1). The second intensity metric, $I_{mean}$, follows similar dependencies on bead size and refractive index as does $I_{max}$. However, for all bead populations the average values and coefficients of variance (CV) of $I_{mean}$ are less than those of Imax as $I_{mean}$ is calculated from the average intensities of the Imax pixel and the surrounding eight pixels.

The observed close correlation between the two optical signatures, Imax and $I_{mean}$ is expected for homogeneous particles having uniform refractive indexes. However, unlike beads, cells have greater internal complexities and local variations of optical properties. For example, in live HeLa cells, an ovarian cancer cell line, the refractive indices of the nucleus, nucleolus and cytosol have been measured using tomographic phase imaging to be 1.355-1.365 RIU, 1.375-1.385 RIU, and 1.36-1.39 RIU, respectively[29]. Considering applications focused on identifying tumor cells in blood, it is useful to also consider those of lymphocytes and monocytes, two populations of white blood cells. Based on light scattering and multiple layer spherical models lymphocytes were found to have a nuclear and cytoplasmic refractive index of 1.43±0.05 RIU and 1.356±0.009 RIU, respectively; whereas monocytes were found to have a nuclear and cytoplasmic refractive index of 1.43±0.04 RIU and 1.348±0.004 RIU, respectively[30]. The above analysis indicates that for same size of cells their internal complexities may differ from each other which in turn may affect the scattered light from cells. For tumor and white blood cells, $I_{max}$ represents the maximum intensity corresponding to the single bright pixel at the core of a focused image hence is primarily affected by the size of the cell due to forward scattering; whereas $I_{mean}$, a 3×3 pixel$^2$ region of the focused image, is expected to be influenced by the optical properties of a region extending throughout both the nucleus and regions of the cytoplasm.

Figure 2G:
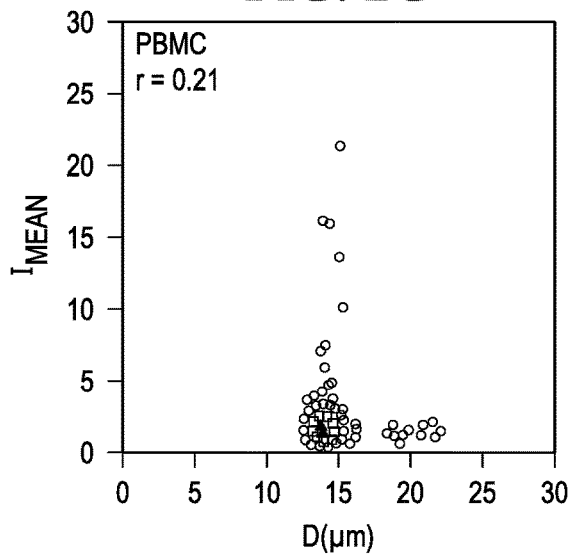
Figure 2H:
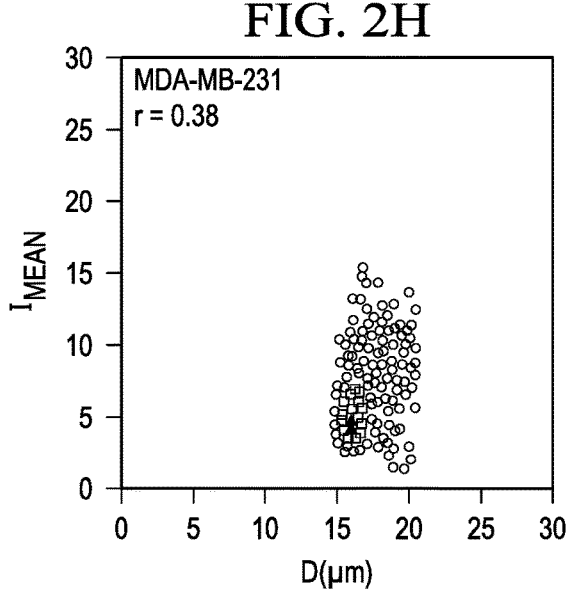
Figure 2I:
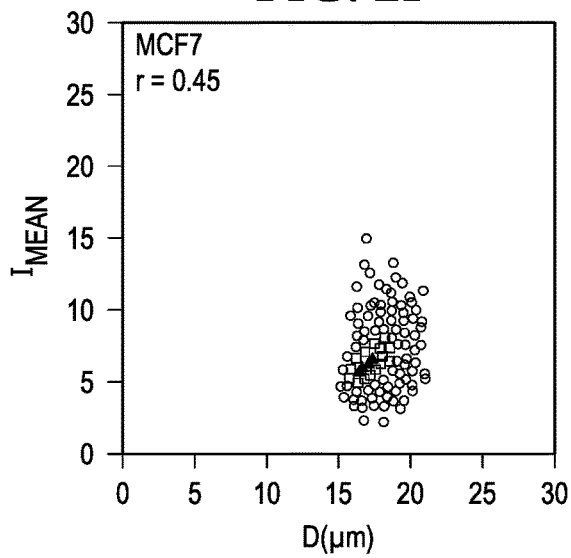

FIGS. 2A-2I are images of binary correlations between the three metrics of size (D), maximum ($I_{max}$) and mean ($I_{mean}$) intensity. Cell types and the correlation coefficient (r) between the metrics are shown as an inset. The number of cells analyzed to generate each plot is 100,000. To further explore the dependencies in cells among the three metrics, D, $I_{max}$ and $I_{mean}$, 100,000 cells from each of the three cell populations were characterized. Specifically, the inventors characterized PBMCs isolated from donor blood through red blood cell lysis and two breast cancer cell lines (MDA-MB-231 and MCF7). Scatter plots suggest a strong relationship between $I_{mean}$ and $I_{max}$ with a covariance quantified as 0.46, 0.87, and 0.79 for PBMC, MDA-MB-213 and MCF7 cells, respectively (FIG. 2A-C). That these correlation coefficients are not closer to 1 support the non-redundant nature of these two intensity metrics in characterizing cells. Further, the correlation coefficients between D and $I_{max}$ (FIG. 2D-F) as well as D and $I_{mean}$ (FIG. 2G-I) are less than 0.5 for all cell three cell populations and is not increased when comparing with D3, further supporting that the optical signatures are not exclusively dictated by cell size.

This focuses on method development that might be readily extended to detecting tumor cells in patient blood. Here, MDA-MB-231 and MCF7 breast cancer cell lines act as models for patient-derived CTCs. Like CTCs, these cell lines have similarly increased average sizes and refractive indices compared to blood-derived cells[31,32]. Although the inventors anticipate applications using inline-DHM to quantify tumor-like cells in patient whole blood, this work focuses on identifying tumor cells among the PBMC sub-fraction of healthy donor blood. A background of the red blood cell lysis derived PBMC sub-population was chosen for preliminary experiments rather than whole blood to allow rapid development of metrics differentiating tumor cells from normal blood while minimizing computational processing required to characterize large numbers of readily differentiated red blood cells.

Figure 3:
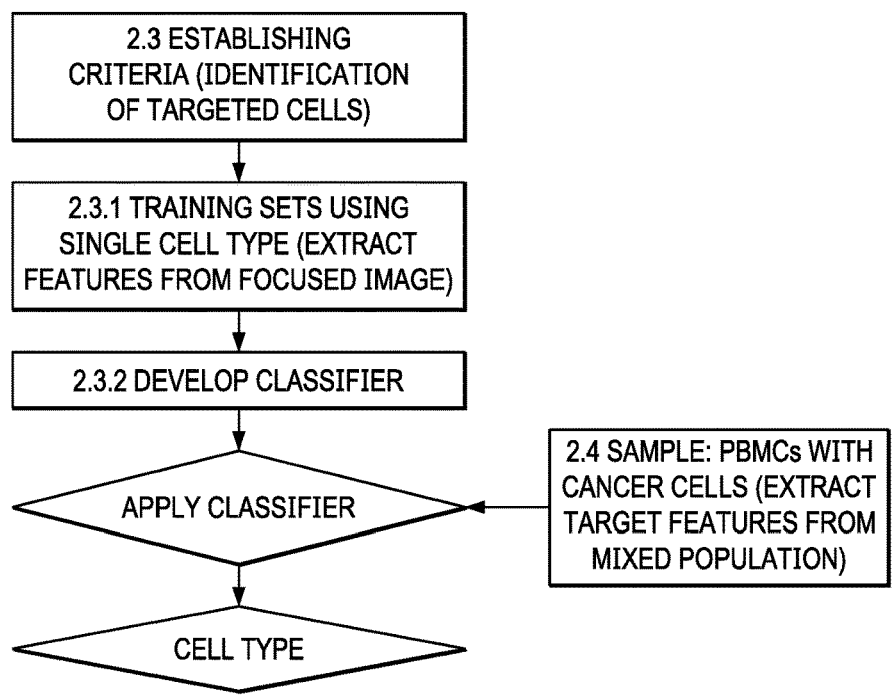
FIG. 3 shows the workflow which is well established within the field of machine learning to develop classifiers from features extracted from the simplified training sets.

FIG. 3 shows a workflow that is well-established within the field of machine learning to develop classifiers from features extracted from the simplified training sets. The inventors used single populations of blood cells including RBCs and PBMCs isolated from donor blood through red blood cell lysis as well as of two breast cancer cell lines (MDA-MB-231 and MCF7) as training sets. Optimized classifiers were then applied to identify cancer cell lines within a background of blood cells.

Figure 4A:
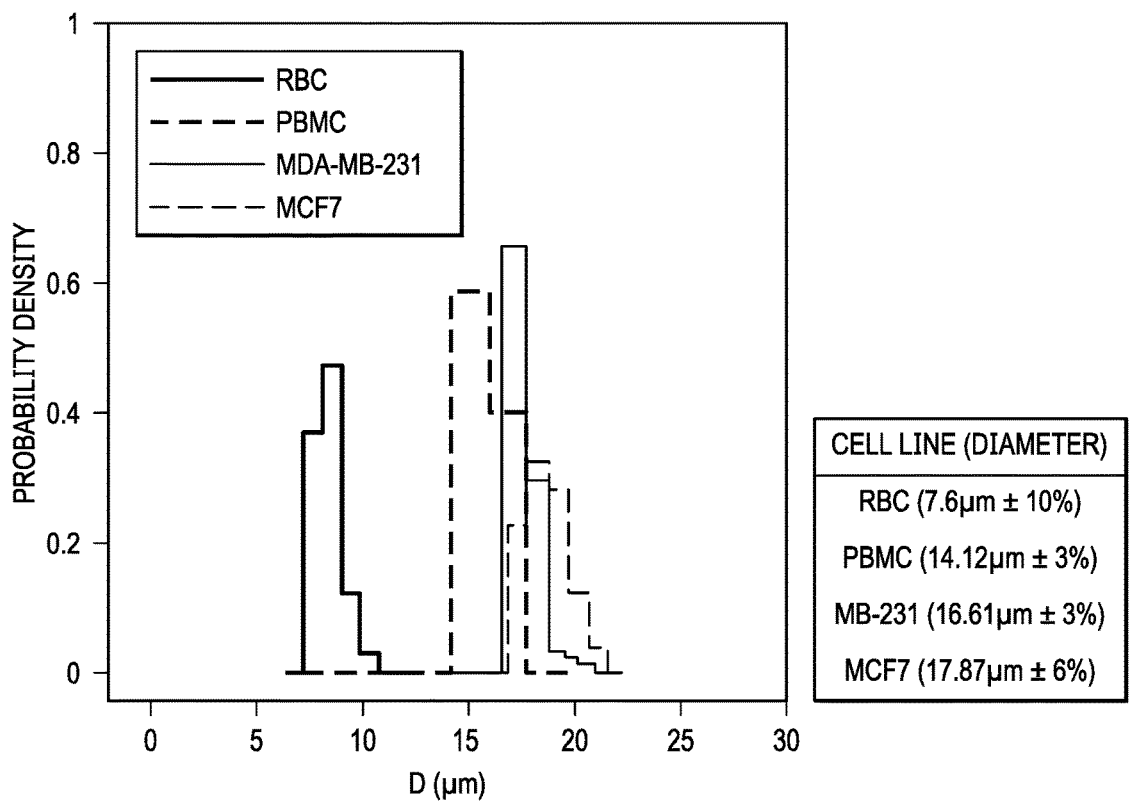
FIGS. 4A-4C show characteristic features of pure populations of different cell types.
Figure 4B:
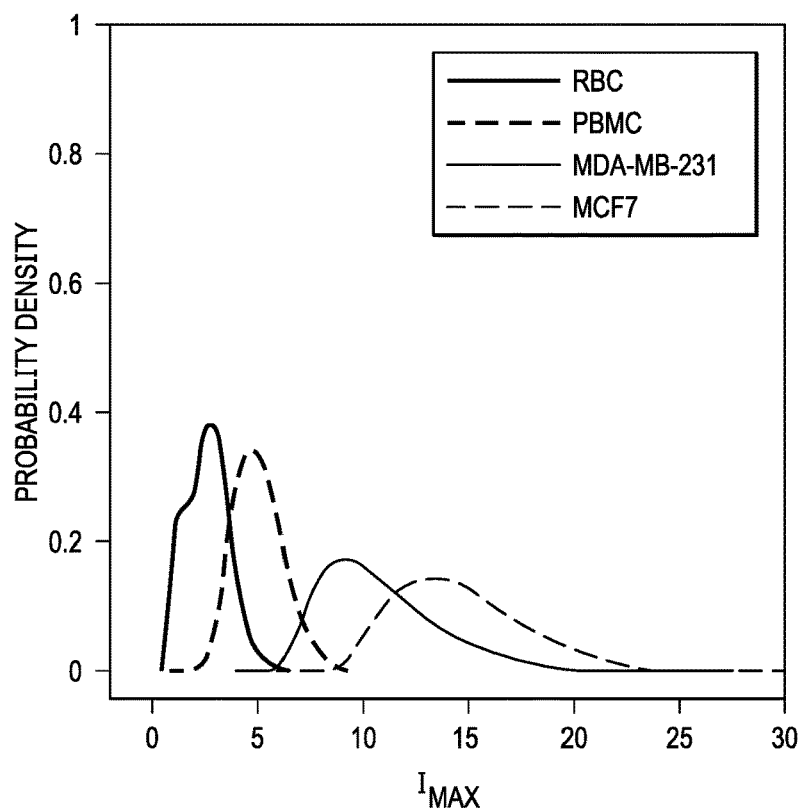
Figure 4C:
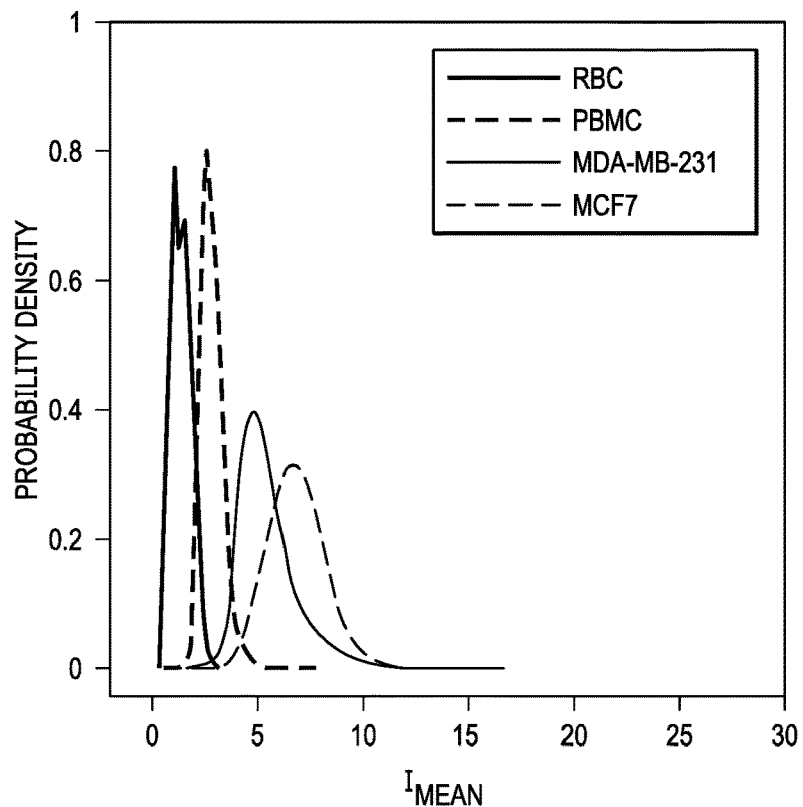

FIGS. 4A-4C show characteristic features of pure populations of different cell types. Probability density with respect to (FIG. 4A) diameter, D, (FIG. 4B) maximum intensity, $I_{max}$, and (C) mean intensity, $I_{mean}$, of different types of pure cellular populations. The data was generated from at least 100,000 cells of RBCs, PBMCs, MDA-MB-231 cells, and MCF7 cells. The inventors extracted the characteristic features of cells from the numerical reconstruction of digital holograms of single populations of blood cells including RBCs, PBMCs and the two cancer cell lines (MDA-MB-231 and MCF7). For each subpopulation, the three metrics: D, I $I_{max}$ and $I_{mean}$ were recorded from 100,000 flowing cells. The average diameters of the cell populations closely follow expected values (FIG. 4A). Literature suggests that the mean diameter across the long axis of disk-like red blood cells is around 8 μm compared to the DHM-recorded average diameter of 7.6 μm. Of note, the 10× magnification employed here generates a 3 to 4 pixel reconstructed image for each RBC making the optical resolution and intensity based characterization insufficient to resolve the asymmetric character of RBCs as the size of each pixel is 2×2 μm$^2$. The mean size of PBMCs is reported to be around 14 μm[33] closely matching the recorded cell diameter of 14.12 μm. Similarly, reported tumor cell diameters fall between 15 and 20 μm[34] compared to recorded average diameters of 16.61 μm and 17.87 μm for MDA-MB-231 and MCF7 cells, respectively.

As established in the previous section, intensity metrics are expected to incorporate aspects of both the cell size and optical properties. Comparing the average value mean ($I_{mean}$) and maximum ($I_{max}$) intensities indicates the strong correlation of cell size with observed intensities. Broadly, the rank order of cell types by increasing diameter mirrors that by both Imax and $I_{mean}$ (FIG. 4). Finally, comparing the overall probability densities with respect to diameter, $I_{max}$ and $I_{mean}$ from pure population of RBCs, PBMCs, MDA-MB-231 and MCF7 supports red blood cells having much smaller average diameters might be readily distinguished from PBMCs and both cancer cell lines. However, it is clear from FIG. 4 that, as would also be expected for patient derived samples, the individual intensity and diameter distributions of the PBMCs and tumor cells are not discrete. The overlapping individual metrics demand further optimization of classification strategies, including those incorporating intensity metrics, to achieve robust cell identification.

The training sets of known cell populations can be used to train classifiers able to identify cells within mixed populations. Each classification strategy balances the tolerance for false positives, the tolerance for false negatives, and computational simplicity where the optimal process is dependent on the end application. For example, screening for CTCs in dilute blood might require an extremely low tolerance for false positives (i.e. blood cells identified as tumor cells) as the great excess of blood cells compared to tumor cells would lead both healthy and normal patients to have a large number of cells classified as tumor cells. Screening on subpopulations enriched in CTCs might favor classification strategies with limited false negatives. In all cases, incorporating multiplexed metrics has the potential to increase overall accuracy, but also risks overfitting the system and unnecessarily complicating downstream processing.

Figure 5A:
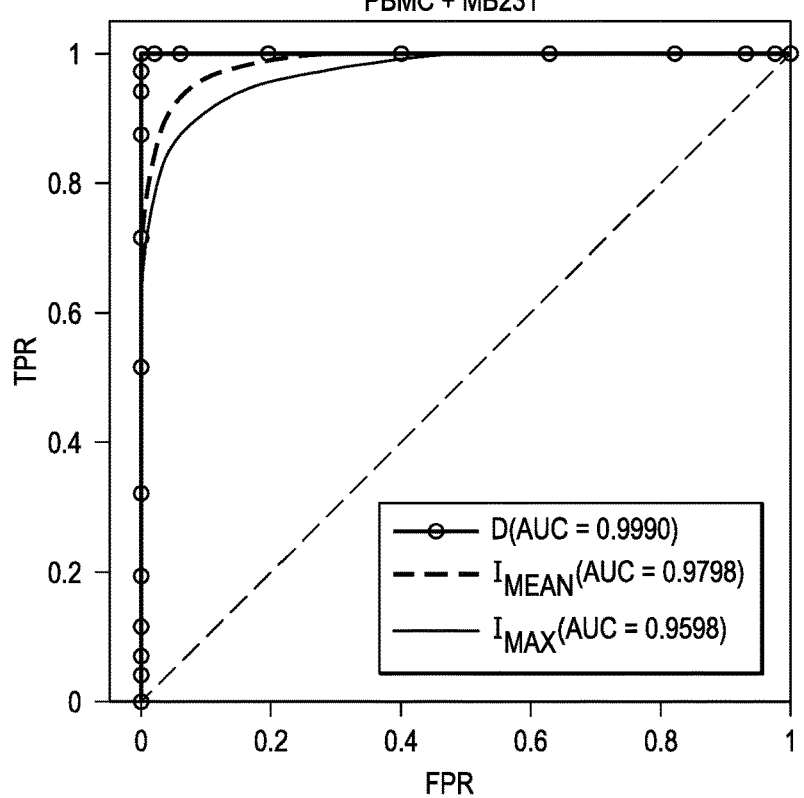
FIGS. 5A-5D are graphs showing the receiver operating characteristics (ROC) curve showing the false positive rate (FPR) versus the true positive rate (TPR) with respect to three characteristic metrics: size (D), mean intensity ($I_{mean}$) and maximum intensity ($I_{max}$).
Figure 5B:
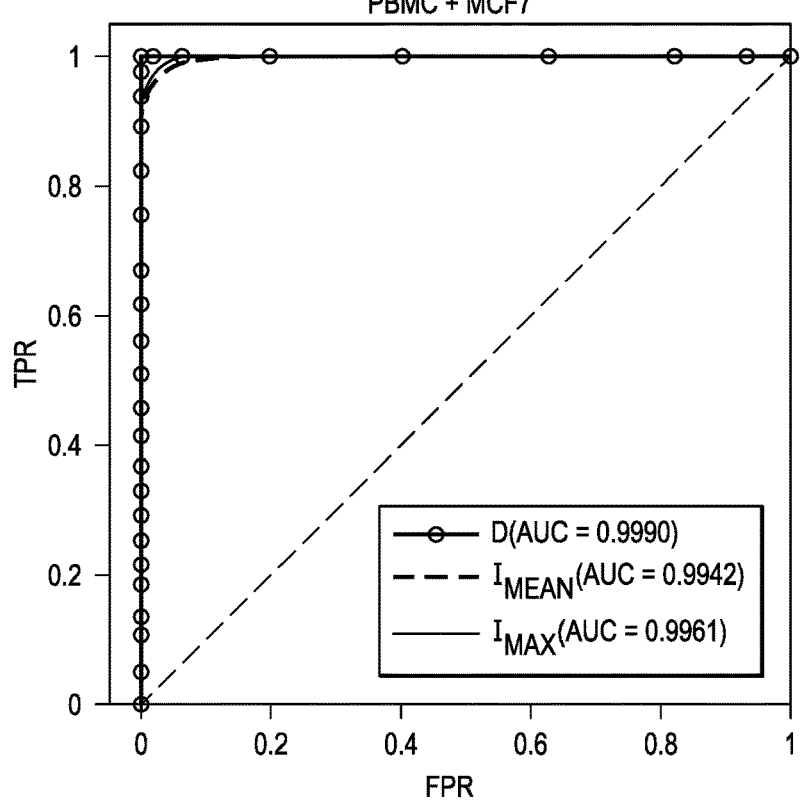
Figure 5C:
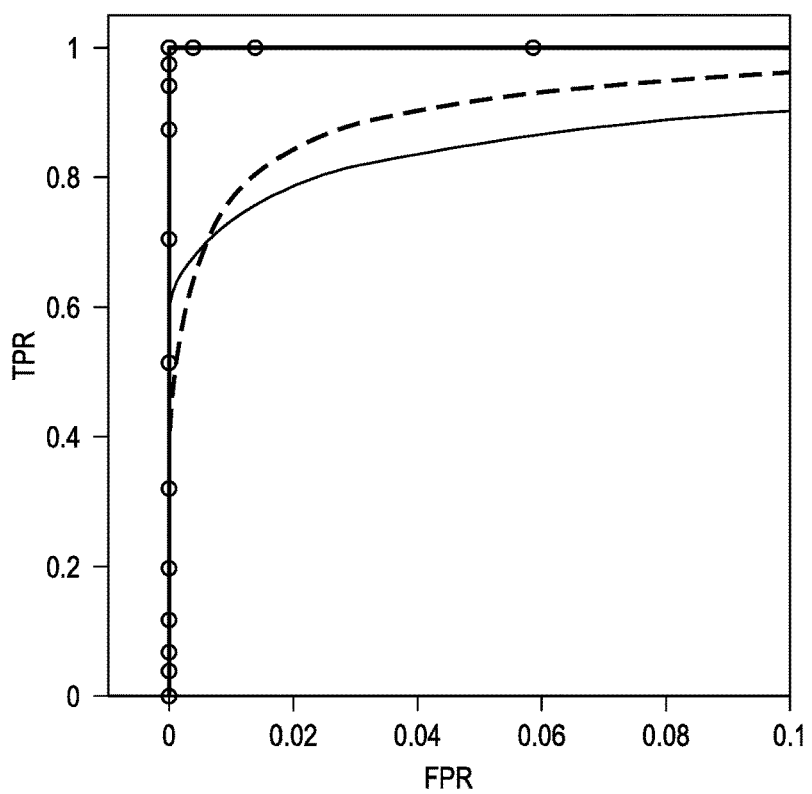
Figure 5D:
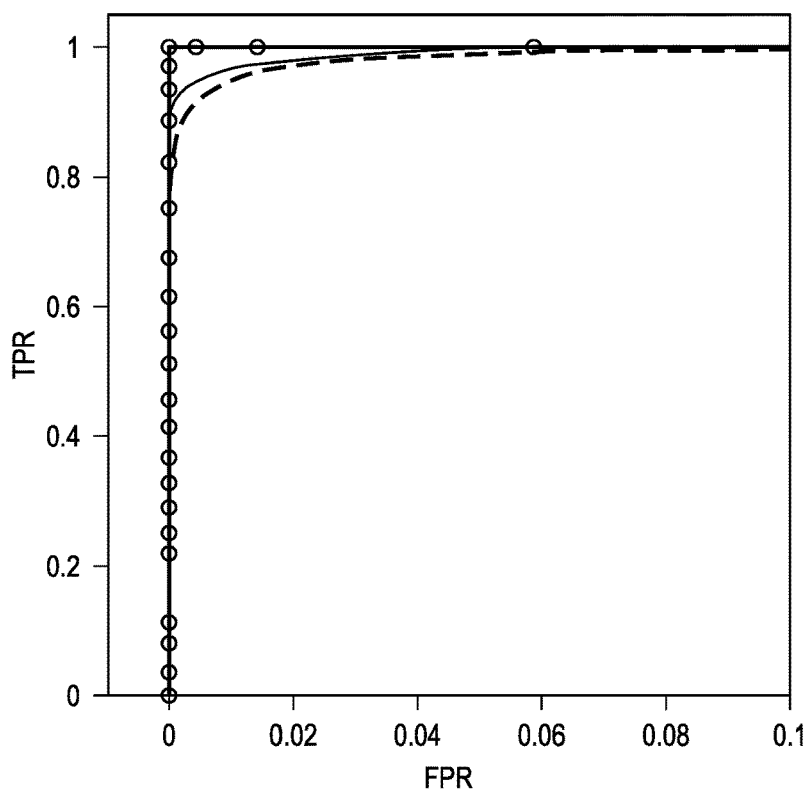

FIGS. 5A-5D are graphs showing the receiver operating characteristics (ROC) curve showing the false positive rate (FPR) versus the true positive rate (TPR) with respect to three characteristic metrics: size (D), mean intensity ($I_{mean}$), and maximum intensity ($I_{max}$). The ROC curve is shown for distinguishing (FIG. 5A) PBMC & MDA-MB-231 and (FIG. 5B) PBMC & MCF7 where the line TPR=FPR corresponds to random guessing. For visual clarity the zoomed-in ROC curves to a false positive rate of 0.1 are presented in (FIG. 5C) and (FIG. 5D) corresponding to (FIG. 5A) and (FIG. 5B) respectively. The inventors first quantify the capabilities of the simple classification strategy, binary classifiers, for differentiating targeted tumors cells among a background of PBMCs. To visualize the classification accuracy, the inventors use a receiver operating characteristic (ROC) curve which is generated by plotting the true positive rate (TPR) and false positive rate (FPR) at various threshold settings. FIGS. 5A and 5B show the ROC curve visually demonstrating the accuracy of each of the three metrics, D, $I_{max}$ and $I_{mean}$ in differentiating PBMCs from each of the cancer cell lines (MDA-MB-231 and MCF7). FIGS. 5C and 5D are zoomed in presentations corresponding to FIGS. 5A and 5B respectively for visual clarity. From these FIGS., it is clear that the area under the curve (AUC) is more than 0.9 for all three characteristic curves of D, $I_{max}$ and $I_{mean}$ for both the populations PBMC & MDA-MB-231 and PBMC & MCF7. This indicates that while diameter is the most robust independent discriminating metric, all three metrics can be used as strong classifiers to identify tumor cells in a lysed blood population of PBMCs with a high TPR and with a very low FPR.

Figures 6A, 6B:
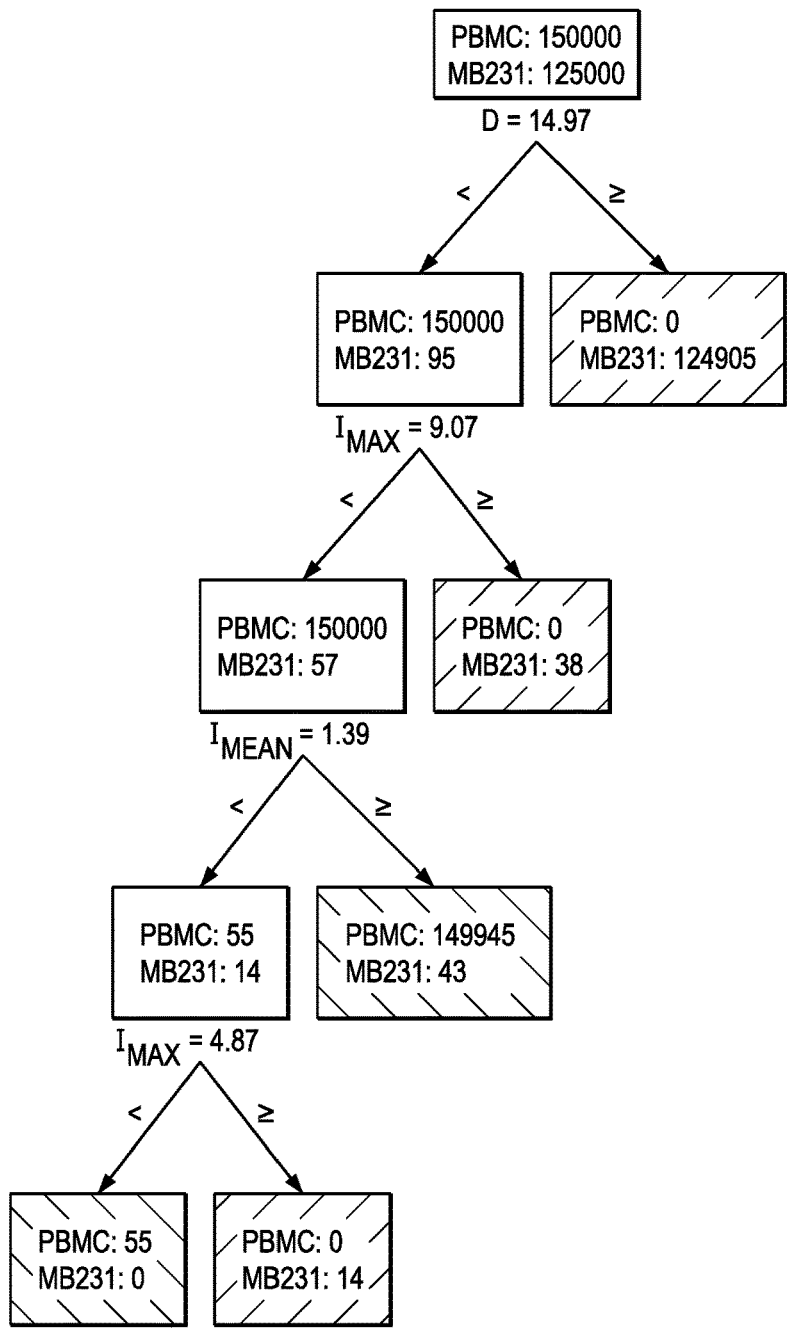
FIGS. 6A-6D illustrate a decision tree based on the CART-algorithm to develop classifiers using the characteristic metrics of size (D), maximum intensity ($I_{max}$) and mean intensity ($I_{mean}$) to discriminate populations of PBMC & MDA-MB-231(MB231) and PBMC & MCF7.
Figure 6C:
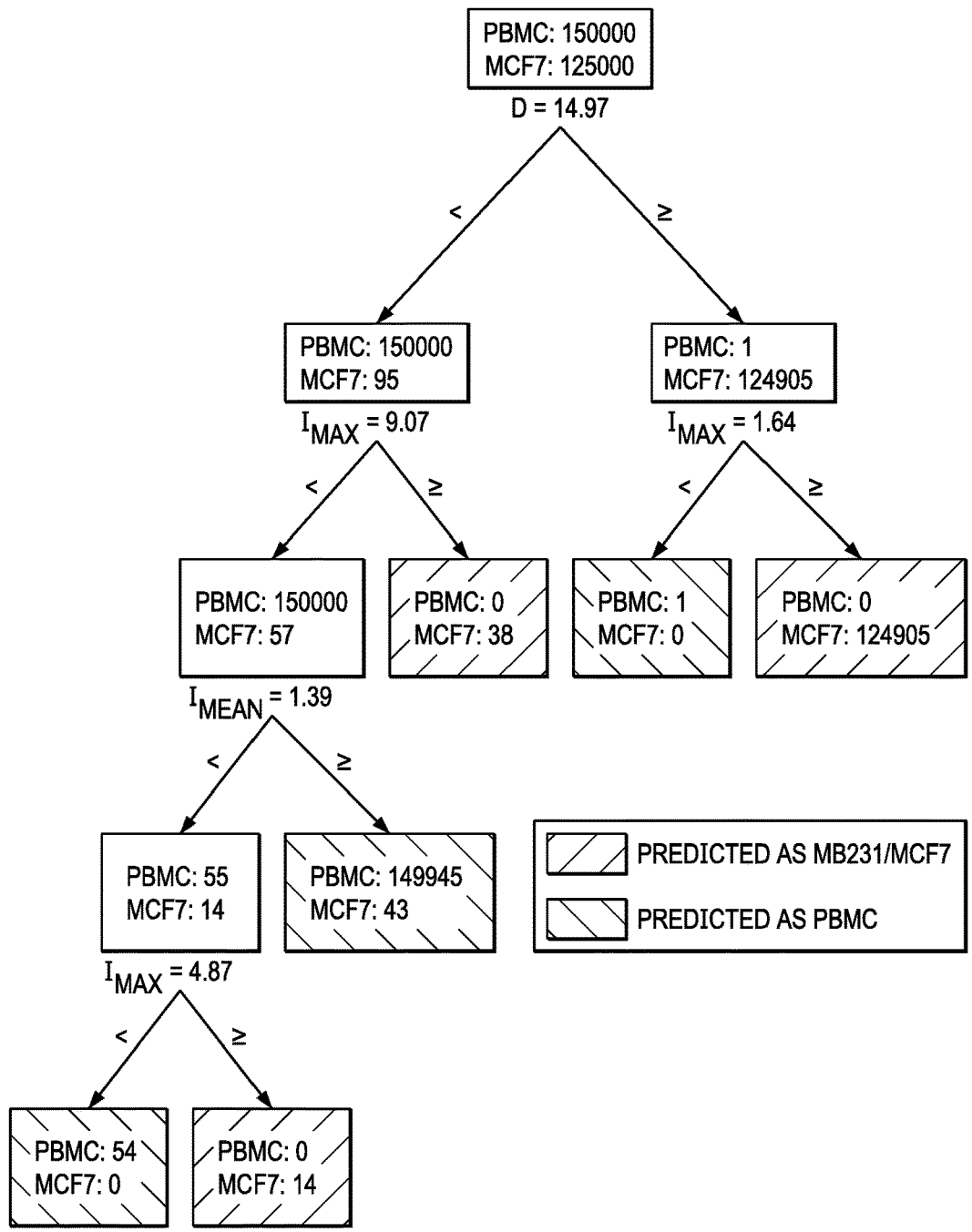
Figure 6D:
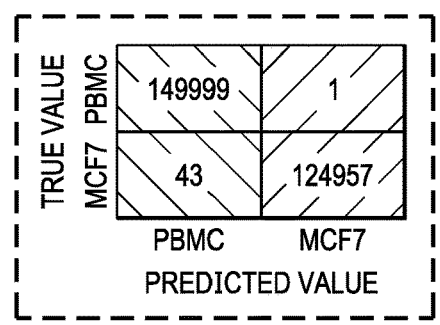

FIGS. 6A-6D illustrate a decision tree based on the CART-algorithm to develop classifiers using the characteristic metrics of size (D), maximum intensity ($I_{max}$) and mean intensity ($I_{mean}$) to discriminate populations of PBMC & MDA-MB-231(MB231) and PBMC & MCF7. (FIG. 6A) & (FIG. 6B) show the decision tree and the predicted values of PBMC and MB231 cells with respect to their true values. Similarly, (FIG. 6C) & (FIG. 6D) show the decision tree and the predicted values of PBMC and MCF7 cells with respect to their true values. Applications requiring more resolved separations are expected to benefit from more developed gating strategies integrating multiple classifiers. FIG. 6 shows one such approach, the decision tree based on the CART-algorithm, to develop a classifier from the pure subpopulations of PBMC & MDA-MB-231 (FIG. 6A) and PBMC & MCF7 (FIG. 6C), respectively. The maximum split limit has been set as 6 for both cases. At every branching point of the tree, the towing method is used to optimize the classifier among three characteristic metrics D, $I_{max}$ and $I_{mean}$. FIG. 6B shows that 124,957 MDA-MB-231 cells out of 125,000 cells within the training set were predicted as true positive and with 0 false positives from 150,000 cells of PBMCs. Similarly, FIG. 6D shows that 124,957 MCF7 cells out of 125,000 cells were predicted as true positives and with only one false positive from the population of 150,000 PBMCs. It can be concluded that the present machine learning algorithm provides high accuracy identifying targeted cells based on their three characteristics, D, $I_{max}$ and $I_{mean}$. As expected from single cell metrics, diameter is the overriding discriminating metric for both decision trees; however, incorporating data from both intensity metrics is necessary for optimal differentiation. The inventors also verified that linear discriminant analysis and support vector machines generated similar improved accuracy over binary discriminants by incorporating all three metrics. In summary, these results suggest the potential for each of the three metrics, D, $I_{max}$ and $I_{mean}$, to support enumeration of tumor cells within a background of blood.

The classification strategies developed above were used to identify breast tumor cells within a background of lysed blood based on the inline-DHM metrics of size, maximum intensity, and mean intensity. In more detail, samples containing crude ACK Lysing Buffer-processed healthy donor blood cells containing white blood cells (WBCs) and residual RBCs at a total cell concentration of 0.45 million/mL were spiked with breast tumor cells (MDA-MB-231 or MCF7) at approximately 100, 50 and 10 tumor cells/mL. Significantly, the blood donor was distinct from the donor used to develop the classifier. In these experiments, each hologram corresponds to measuring approximately 100 cells. Since the inventors acquired 100 holograms per second for 45 s, the inventors processed 4500 holograms and characterized ≈450,000 cells per spiked sample, or equivalently 10,000 cells per second.

Figure 7B:
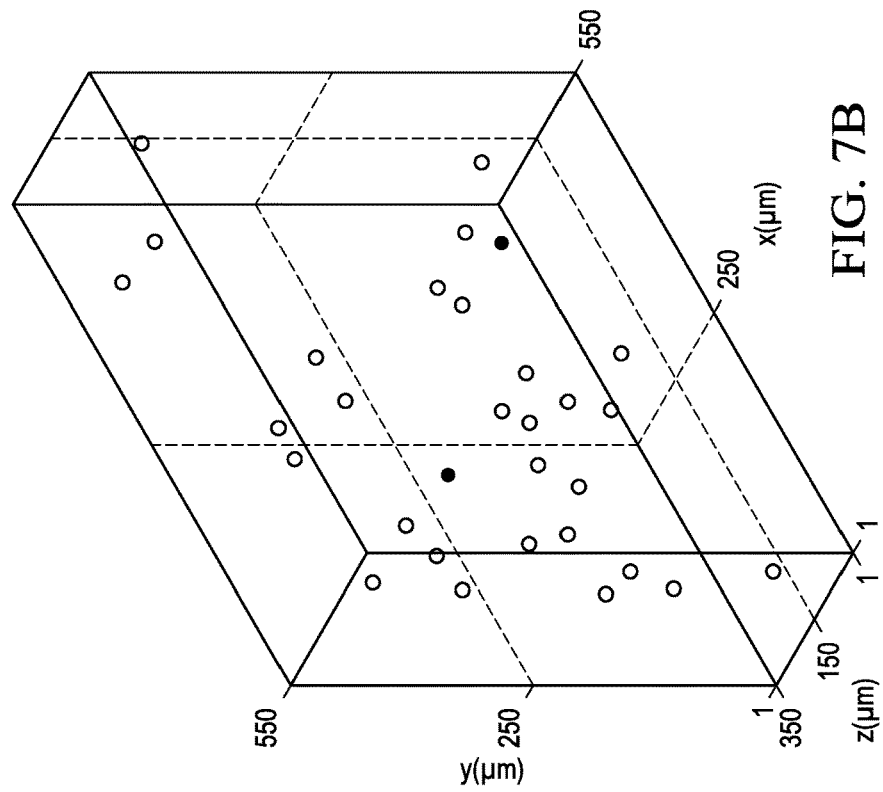
Figure 7A:
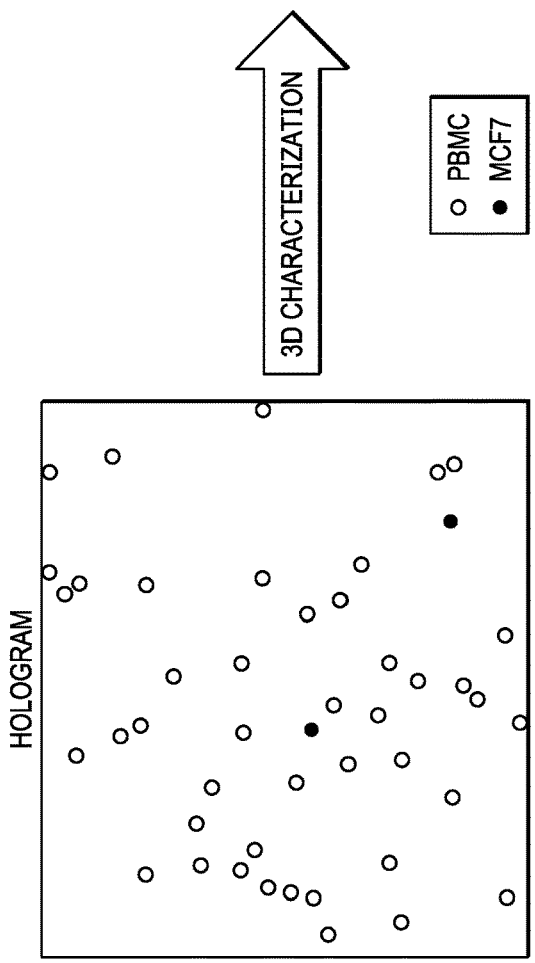

FIGS. 7A-7D are graphs of identification and enumeration of tumor cells spiked in lysed whole blood. (FIG. 7A) The hologram of lysed blood sample spiked with MCF7 cells, (FIG. 7B) 3D model generated from numerical reconstruction of single hologram in (FIG. 7A). Identification of spiked cells (FIG. 7C) MDA-MB-231 and (FIG. 7D) MCF7 cells at three different concentrations of spiking in the lysed blood populations of 0.45 million/mL. With respect to computational analysis, each hologram was numerically reconstructed and the position, size, and intensity of each cell were determined. FIG. 7A shows the cropped hologram (500×500 µm²) of cells flowing through the channel, from the original hologram of size 1024×1024 µm². The decision classifier developed through training data (FIG. 6) was used to differentiate blood cells from each cancer cell line enabling a 3D reconstruction of the location and inferred identity of the mixed cells within the channel (FIG. 7B). This single snap-shot shows the location of thirty cells classified as PBMCs (red) and two cells classified as MCF7 cells (blue) flowing along the x-direction within the rectangular microfluidic device (FIG. 7B). The inventors note that the laminar nature of flow introduces the complication of counting slower cells multiple times in sequential frames. The multiple counting of cells has been eliminated using the streamline coordinates, y and z, of reconstructed cells. The detailed process of eliminating multiple counts has been reported in the previous work[19]. FIGS. 7C and 7D report the number of feed (input) and the identified (output) breast tumor cells, MDA-MB-231 and MCF7 respectively. At a spiked concentration of C=0 tumor cells, 6 cells were identified as false positive out of 450,000 reconstructed lysed blood cells using classifier defined for MDA-MB-231 in FIG. 6A whereas; using the classifier for MCF7 as defined in FIG. 6B, no false positives were identified out of 450,000 reconstructed lysed blood cells. At spiked concentrations of C=10, 50, and 100, for each breast tumor cell line the numbers of feed (input) cells are in close agreement with those of the identified (output) cells (FIGS. 7C, 7D, Table 2).

Table 2 shows a comparison of minimum detectable spike in amount to non-spiked detection is presented. The concentration of spiked tumor cells is targeted to be 10, 50, and 100 cells/mL of MCF7 and MDA-MB-231 each. The classification strategy corresponding to MCF7 and MDA-MB-231 has also implemented to non-spiked concentration (i.e. C=0 cells/mL) to suggest a minimum detection limit. The total analyzed sample volume and number of cells (tumor cells+PBMCs) is 1 mL and 450,000 respectively.

TABLE 2

| Cell Line | Input Concentration (Cells/mL) | Spiked Cancer Cells in PBMCs from Donor 1 | | | | |
|---|---|---|---|---|---|---|
| | | $n_1$ | $n_2$ | $n_3$ | Mean | Standard deviation |
| MCF7 | 0 | 0 | — | — | 0 | 0 |
| | 10 | 17 | 4 | 18 | 13 | 8 |
| | 50 | 17 | 63 | 10 | 30 | 29 |
| | 100 | 67 | 73 | 113 | 84 | 25 |
| MDA-MB231 | 0 | 6 | — | — | 0 | 0 |
| | 10 | 21 | 26 | 2 | 16.33 | 12.66 |
| | 50 | 59 | 8 | 63 | 43 | 31 |
| | 100 | 123 | 146 | 61 | 110 | 44 |

Differences in exact values are attributed to challenges in making accurate stock solutions due to manual counting errors using a hemocytometer at low concentrations and dilutions of a stock solution[35] as well as variable cell settling prior to imaging sub fractions of the prepared solutions. That differences between the intended and observed cell number do not vary systematically supports this hypothesis of random error. The low false positive rate cancer cells identified in the PBMC sample was replicated in blood processed from two additional donors (Table 3).

Table 3 shoes the detection of tumor cells in lysed blood of three different donors in non-spiked condition is presented. The classification strategy corresponding to MCF7 and MDA-MB-231 has been implemented to non-spiked concentration (i.e. C=0 cells/mL) to suggest a minimum detection limit. The total analyzed sample volume and number of cells (tumor cells+PBMCs) is 1 mL and 450,000 respectively.

TABLE 3

| Cell Line | Input Concentration (Cells/mL) | Donor-1 | Donor-2 | Donor-3 | Mean | Standard deviation |
|---|---|---|---|---|---|---|
| MCF7 | 0 | 0 | 3 | 1 | 1.33 | 1.5 |
| MDA-MB231 | 0 | 6 | 3 | 0 | 3 | 3 |

In this work, the inventors have introduced inline-DHM as a label-free imaging platform appropriate for the identification and characterization of cells in bulk flow, with a focus on detecting tumor cells in blood. The inventors have established three suitable metrics, cell diameter, $I_{max}$ and $I_{mean}$, for characterizing blood components and tumor cells. The inventors applied machine-learning approaches to identify tumor cells within a background of blood cells. Testing the classifier on the distinct blood sample used for the spiked experiments resulted in, at most, 0.001% false positives (blood cells identified as tumor cells). Below the inventors discuss how the existing approach can be advanced to achieve significantly more throughput and also present avenues for configuring DHM technology for analyzing real CTCs in patient samples. In this study, the inventors analyzed ≈100 cells per 3D image volume and 4500 holograms, achieving a throughput of 450,000 cells per sample. In the future, it is possible to increase the throughput of cellular analysis to $10^6$-$10^7$ cells per sample. The main limiting factors for increasing throughput is the camera system needed to record/store the holograms and the computational time required for numerical reconstruction. In this work, the inventors used a CMOS camera (Phantom v.310) to record at 100 fps and store 4500 holograms per sample. The 16 GB RAM available on this camera can be used to store as many as 20,000 holograms, indicating that $2 \times 10^6$ cells can be analyzed with the existing hardware. However, the time-consuming step then becomes the computational processing of the holograms. Here, the inventors used a standard desktop computer (3.6 GHz processor, 8 GB RAM) to analyze the 4500 holograms, which took ≈7 s per hologram and 8.75 hours per sample. Rather than a single processor, by pursuing distributed computing, along with optimized reconstruction algorithms, the inventors anticipate the computational analysis time can be reduced significantly. Given that the computational processing can be done off-line and is not labor intensive, the label-free approach out-competes tedious immunofluorescence staining methods to detect cancer cells in mixed populations.

Moving DHM towards analyzing CTCs in cancer patient samples: Looking towards applications targeting patient screening, it is generally accepted that at least 3 mL of patient blood needs to be processed to achieve reliable information about CTCs where whole blood is estimated to contain approximately 4-5×$10^9$ RBCs and 5-11×$10^6$ WBCs per mL. In this study, the inventors have used lysed blood and since the sample injection flow rate is 1400 μL/min, the volume processing rate is 23 μL/s. Sample preparation involving lysis of RBCs in 3 mL of patient blood yielded ≈$10^7$ WBCs/mL in 22 mL, which is imaged by DHM in ≈50 minutes @ 100 fps. The inventors note that the injection flow rate or sample processing rate can be increased to beyond what the inventors used in this embodiment, in which case the camera frame rate would need to be increased. This will also lead to reduced image acquisition time.

Rather than lysing blood, non-invasive CTC enrichment strategies can also be pursued in combination with DHM detection. For example, RBCs can be removed through deterministic lateral displacement (DLD) debulking in which fluid under laminar flow regimes is passed through asymmetric micropillar arrays in a microfluidic device[36,37]. Samples might be further enriched by additionally removing a subpopulation of PBMCs through a variety of inertial techniques such as those incorporated into spiral devices using Dean Flow Fractionation (DFF)[10,38], the Vortex Chip[7], and the multi orifice flow fractionation (MOFF) microfluidic device[14]. Using the above enrichment methods, it is useful to estimate the amount of image acquisition that is needed to DHM-process the entire sample volume. Integrating the DFF[38] method which enriches the sample by 10[9] fold over RBCs and 10[3] fold over WBCs, 3 mL of injected blood sample results in ≈25 mL of enriched sample containing 1300 WBCs/mL. Given the sample processing rate of 23 µL/s the inventors can DHM-image the 25 mL in 19 minutes @ 100 fps—which is 3× less time than the lysis method. Processing methods such as the Vortex Chip[7], which recover highly enriched samples in small volumes (<1 ml) might be DHM-imaged in <60 seconds. Finally, in this study the inventors have demonstrated detection of 10 tumor cells/mL at a false positive rate of 0.001%. In the patient samples, the inventors will have a need to detect 10× lower number of tumor cells. The accuracy of detection can be improved by incorporating additional metrics (e.g. gradient of intensity) from the data-rich holograms. Thus, the DHM technology has the potential to robustly identify CTCs and classify their subpopulations without destructive processing and labeling of cells. This embodiment, analyzing donor blood and cancer cell lines suggest that the combined DHM-derived signatures of single cell diameters and intensity profiles provide a new and promising metric for differentiating tumor derived cells from background hematopoietic cell types. Using these metrics, inline-DHM provides rapid, highly accurate, platform-flexible, and label-free discrimination of tumor cells in patient blood. Moving beyond CTC applications, the present invention provides a generic label-free method for detecting target cells in mixed populations, which is useful in cytopathology, drug resistance, and identification of rare stem cells. Microfluidic Device Fabrication. The microfluidic channels of width, w=1000 µm, and height, h=350 µm, were fabricated using soft lithography[39]. Negative photoresist (SU-8 2050) were used to make the mold. Polydimethyl siloxane (PDMS) prepolymer and curing agent were mixed in a 10:1 ratio, degassed, poured on the mold and cured for a minimum of two hours at 65° C. The PDMS replica was cut with a scalpel and peeled. Inlet and outlet reservoirs were defined by punching holes and the channel was irreversibly bonded to a glass slide 25 mm×75 mm×1 mm; Fisher) after exposing the bonding surfaces of the PDMS device and glass slide to plasma for 2 minutes.

For bead validation assays, polystyrene beads (Polyscience Inc., NIST traceable polystyrene beads) and silica beads (Corpuscular Inc., Monodisperse Silica Microspheres) of mean diameters of 8 and 15 µm were used. Beads were diluted into phosphate buffered saline to a final concentration of 0.45 million beads per ml prior to characterization. For single cell type characterization tumor cell lines MDA-MB-231 (passage 9, purchased from ATCC, Manassas, Va.) and MCF-7 (passage 10, provided by Dr. Lauren Gollahon at Texas Tech University) were cultured in DMEM media supplemented by 10% fetal bovine serum (FBS), 1% penicillin-streptomycin solution (Gibco) and 1 nM sodium pyruvate. Prior to DHM imaging, adherent cultured cells were detached by incubating with trypsin/EDTA solution, neutralized with serum and suspended in phosphate buffered saline. Cells were filtered through a 30 µm pre-separation filter (Miltenyi Biotec) and adjusted to the designated concentrations by further dilution with phosphate buffered saline. Whole human blood was obtained from consenting healthy donors under IRB-approved protocols and processed three days after blood donation. RBCs were characterized as a concentrated subpopulation purified from platelets and white blood cells using Ficoll-Paque with SepMate separation inserts (Stemcell Technologies) as directed by manufacturers. WBCs were isolated from whole blood using ACK Lysing Buffer (Life Technologies) as directed by manufacturer including a secondary lysing step to support more complete RBC removal. Cancer cell lines were cultured on tissue culture polystyrene using standard tissue culture procedures and imaged within one hour after trypsin mediated detachment. Suspensions of cancer cell lines or blood components were filtered through a 30 µm filter and diluted to approximately 0.45 million cells/mL in PBS prior to DHM processing. More than 100,000 cells were processed for each sample.

Details of the Digital Holography Microscopy set up are identical to those described in the previous study[19]. Briefly, as shown in FIG. 1A the in-line DHM arrangement consists of a laser, a spatial filter and collimator assembly, and an inverted optical microscope (IX-71, Olympus Inc.). A He—Ne laser (10 mW, λ, =0.6328 µm, Thorlabs) is used as a light source, operating in continuous wave (CW) mode. The laser beam is filtered and expanded by a spatial filter assembly consisting of a microscope objective (10×, NA=0.25; Thorlabs) and a pinhole (25 µm diameter). The expanded beam is then collimated using a plano-convex lens (focal length, f=100 mm, Thorlabs). The diameter of the collimated beam is approximately 5 mm. This collimated beam of laser light illuminates cells or beads flowing in the microfluidic channel. The flow through the channel is generated by a syringe pump (KD Scientific). The cross-sectional dimensions of the channel are 1000(y)×350(z) µm². The 2D hologram of cells or beads is generated in the focal plane of the microscope objective (M=10×, NA=0.25; Thorlabs) of the optical microscope. The magnified image of the hologram is recorded on a CMOS camera (Phantom v310, Vision Research) at a resolution of 512×512 (20 µm/pixel) and 12-bit gray level quantization. The influence of DHM recording parameters on accuracy of determining axial position and scattered intensity are described in the previous work 19.

The recoded holograms were transferred to a computer for numerical reconstruction and data analysis. Detailed reconstruction methodology for characterization of particles[24-26] and of cells is described in the previous work[19]. The inventors implemented numerical reconstruction procedure in MATLAB, using a standard desktop computer (Intel® Core™ i7-4790 @3.60 GHz, RAM: 8.00 GB). The processing time is about 1.94 hours to analyze 1000 holograms. The present invention provides a first-generation in-line DHM cytometer which is capable to enumerate cells in bulk flow and finger-printing cells based on three features—size, maximum intensity and mean intensity of focused image of cells obtained from numerical reconstruction of recorded hologram of cells. The inventors demonstrated the capacity to enumerate and fingerprint more than 450,000 cells at the rate of 10,000 cells/s and highlighted the power of the label-free and high throughput technology by characterizing breast tumor cell lines with different metastatic potentials and distinguishing drug resistant ovarian cancer cells from their parental cell line.

FIGS. 8A and 8B are images of parallelize DHM cytometry for drug response analysis. The present invention provides for analyzing multiple samples simultaneously using in-line DHM.

The method involves using a microfluidic device with multiple inlets to flow different samples adjacent to each other as shown in FIG. 8A. Since the flow is laminar, there is no mixing and identity of each sample is encoded spatially into the microfluidic device. Integrating DHM into this multi-inlet device, the inventors can capture holograms where each hologram contains information of the multiple samples that are spatially segregated. This multiplexed DHM analysis approach has several areas of application, as discussed below. FIG. 8A is an image showing a multiple entry microfluidic device for parallel loading of multiple samples. Red arrows indicate the recording window for DHM cytometry for drug response analysis. FIG. 8B is a graph showing a dose-dependent cytotoxicity of the doxorubicin for the breast cancer cell line MCF-7 using standard epifluorescence microscopy. Parallel analysis of samples is required in many applications in drug screening, consumer industry and biotechnology. For example, in drug screening there is a need to conduct dose response analysis where different drug concentrations are used to test their impact on the viability of cells (see FIG. 8B for viability analysis using standard fluorescence imaging). To achieve parallel analysis, cells treated with different doses of drug can be introduced into the multi-inlet device and label-free DHM can be used to obtain dose-response curves. Cell culture and drug treatment can also be conducted in the inlet wells of the device or additional microfluidic devices can be daisy-chained prior to DHM interrogation.

Figure 9A:
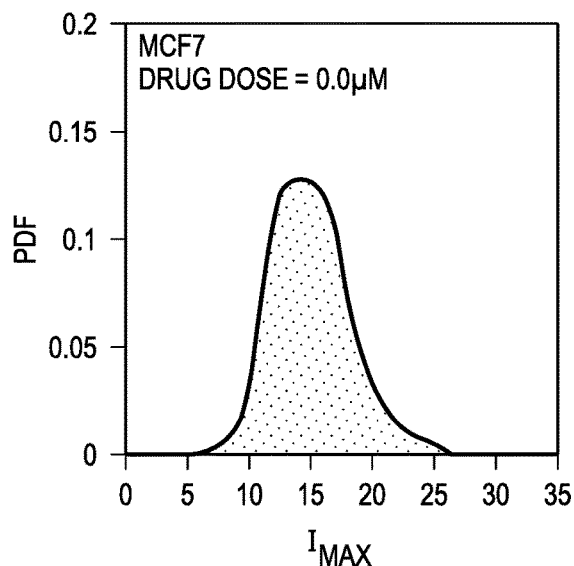
FIGS. 9A-9D are graphs of the in line DHM cytometry for drug response analysis.
Figure 9B:
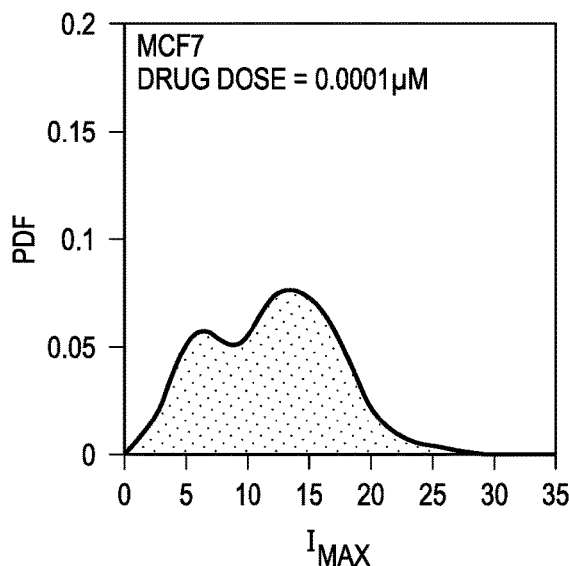
Figure 9C:
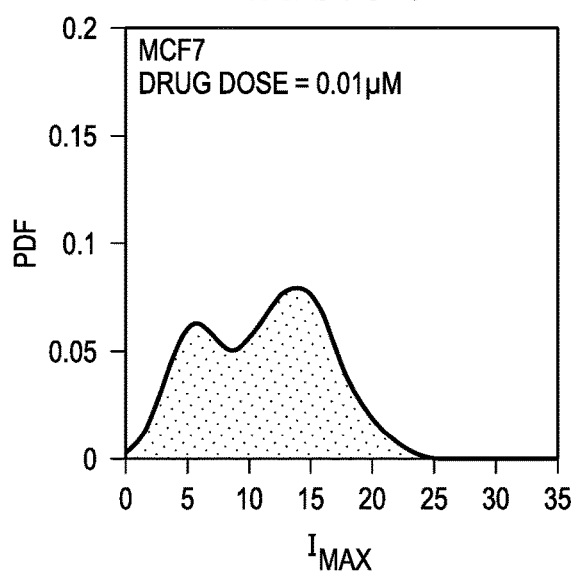
Figure 9D:
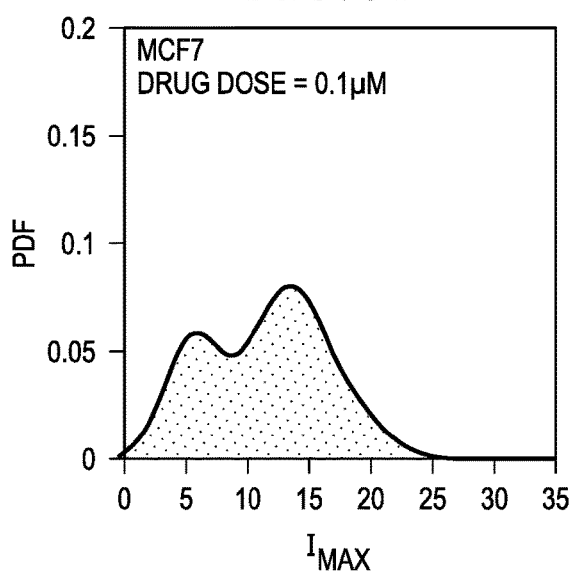

FIGS. 9A-9D demonstrate the capability and sensitivity of DHM cytometer to respond to the effect of anti-cancer drug (doxorubicin) dose to breast cancer cells MCF7. FIGS. 9A-9D are graphs of the inline-DHM cytometry for drug response analysis. The probability distribution corresponding to maximum intensity ($I_{max}$) of center pixel of focused image of breast cancer cells (MCF7) at different doses of doxorubicin (FIG. 9A) 0.0 µM, (FIG. 9B) 0.0001 µM, (FIG. 9C) 0.01 µM, and (FIG. 9D) 0.1 µM. When the cells are treated with drug, each cell responds differently. Some cells are susceptible to the drug and others resist it. As the dose of the drug increases more and more cells are affected and they start losing viability. FIGS. 9A-9D show how the maximum intensity ($I_{max}$) is affected as MCF-7 cells are treated with different drug concentrations. FIG. 9A shows $I_{max}$ distribution for normal cells. When the cells are treated with 0.0001 µM doxorubicin some are affected and their peak intensity shifts to lower values (FIG. 9B). Similarly, as the drug dose increases to 0.01 and 0.1 µM, FIG. 9C and FIG. 9D demonstrate that the number of cells showing lower intensity ($I_{max}$) increases. This study demonstrates that DHM is sensitive to capture the response of drugs in a tumor cell population. Protocol adopted to obtain low concentration of spiked tumor cells. PBMCs were isolated from whole blood using ACK Lysing Buffer following manufacturer protocol. Suspensions of blood components were filtered with a 30 µm filter and diluted in PBS to a final concentration 0.45 million cells/mL. Adherent tumor cell lines, MDA-MB-231 and MCF-7, were cultured to 60-80% confluence, trypsinized using standard protocols, resuspended in PBS (1 million cells/ml), and serially diluted to 1000 cells/mL. For both MD-MBA-231 and MCF 7 samples, cancer cell suspensions were spiked in technical triplicate into PBMC suspensions (2 mL) at 20, 100 and 200 µL cancer cell suspension for target concentrations of 10, 50 and 100 cancer cells per mL. Finally, 1 mL of sample was analyzed corresponding to each data point. The counting of cells was performed by hemocytometer.

It is contemplated that any embodiment discussed in this specification can be implemented with respect to any method, kit, reagent, or composition of the invention, and vice versa. Furthermore, compositions of the invention can be used to achieve methods of the invention. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the present invention, spirit and scope of the invention. All such similar substitutes and modifications apparent to those skilled in the art are deemed to be within the spirit, scope and concept of the invention as defined by the appended claims.

REFERENCES

1 Maheswaran, S. & Haber, D. A. Circulating tumor cells: a window into cancer biology and metastasis. *Curr Opin Genet Dev* 20, 96-99, doi:10.1016/j.gde.2009.12.002 (2010).

2 Maheswaran, S. et al. Detection of mutations in EGFR in circulating lung-cancer cells. *New England Journal of Medicine* 359, 366-377 (2008).

3 Yu, M., Stott, S., Toner, M., Maheswaran, S. & Haber, D. A. Circulating tumor cells: approaches to isolation and characterization. *The Journal of cell biology* 192, 373-382, doi:10.1083/jcb.201010021 (2011).

4 Pantel, K. & Speicher, M. R. The biology of circulating tumor cells. *Oncogene* 35, 1216-1224, doi:10.1038/onc.2015.192 (2016).

5 Ferreira, M. M., Ramani, V. C. & Jeffrey, S. S. Circulating tumor cell technologies. *Mol Oncol* 10, 374-394, doi:10.1016/j.molonc.2016.01.007 (2016).

6 Harouaka, R. A., Nisic, M. & Zheng, S.-Y. Circulating tumor cell enrichment based on physical properties. *Journal of laboratory automation* 18, 455-468 (2013).

7 Che, J. et al. Classification of large circulating tumor cells isolated with ultra-high throughput microfluidic Vortex technology. *Oncotarget* 7, 12748-12760 (2016).

8 van der Toom, E. E., Verdone, J. E., Gorin, M. A. & Pienta, K. J. Technical challenges in the isolation and analysis of circulating tumor cells. *Oncotarget* 7, 62754-62766 (2016).

9 Reategui, E. et al. Tunable nanostructured coating for the capture and selective release of viable circulating tumor cells. *Adv Mater* 27, 1593-1599, doi:10.1002/adma.201404677 (2015).

10 Warkiani, M. E. et al. Slanted spiral microfluidics for the ultra-fast, label-free isolation of circulating tumor cells. *Lab on a Chip* 14, 128-137 (2014).

11 Fang, Y. Label-free drug discovery. *Front. Pharmacol.* 5, 52, doi:10.3389/fphar.2014.00052 (2014).

12 Aceto, N. et al. Circulating tumor cell clusters are oligoclonal precursors of breast cancer metastasis. *Cell* 158, 1110-1122, doi:10.1016/j.cell.2014.07.013 (2014).

13 Zhang, J. et al. Fundamentals and applications of inertial microfluidics: a review. *Lab Chip* 16, 10-34, doi:10.1039/c5lc01159k (2016).

14 Moon, H. S. et al. Continual collection and re-separation of circulating tumor cells from blood using multi-stage multi-orifice flow fractionation. *Biomicrofluidics* 7, 14105, doi:10.1063/1.4788914 (2013).

15 Bagnall, J. S. et al. Deformability-based cell selection with downstream immunofluorescence analysis. *Integrative Biology* 8, 654-664 (2016).

16 Mitra, R., Chao, O., Urasaki, Y., Goodman, O. B. & Le, T. T. Detection of lipid-rich prostate circulating tumour cells with coherent anti-Stokes Raman scattering microscopy. *BMC Cancer* 12, 540, doi:10.1186/1471-2407-12-540 (2012).

17 Shim, S. et al. Antibody-independent isolation of circulating tumor cells by continuous-flow dielectrophoresis. *Biomicrofluidics* 7, 11807, doi:10.1063/1.4774304 (2013).

18 Li, P. et al. Acoustic separation of circulating tumor cells. *Proceedings of the National Academy of Sciences* 112, 4970-4975 (2015).

19 Singh, D. K., Ahrens, C. C., Li, W. & Vanapalli, S. A. Label-free fingerprinting of tumor cells in bulk flow using inline digital holographic microscopy. *Biomed. Opt. Express* 8, 536-554, doi:10.1364/BOE.8.000536 (2017).

20 Kim, M. K. Principles and techniques of digital holographic microscopy. *J. of Photonics for Energy*, 018005, doi:10.1117/6.0000006 (2010).

21 Goodman, J. W. *Introduction to Fourier Optics.* (McGraw-Hill, 1968).

22 Kreis, T. *Handbook of Holographic Interferometry Optical and Digital Methods.* (WILEYVCH Verlag GmbH & Co., 2005).

23 Choi, Y.-S. & Lee, S.-J. Three-dimensional volumetric measurement of red blood cell motion using digital holographic microscopy. *Appl. Opt.* 48, 2983-2990 (2009).

24 Singh, D. K. & Panigrahi, P. K. Three-dimensional investigation of liquid slug Taylor flow inside a microcapillary using holographic velocimetry. *Experiments in Fluids* 56, 1-15, doi:10.1007/s00348-014-1863-9 (2015).

25 Singh, D. K. & Panigrahi, P. K. Automatic threshold technique for holographic particle field characterization. *Applied Optics* 51, 3874-3887, doi:10.1364/AO.51.003874 (2012).

26 Singh, D. K. & Panigrahi, P. K. Improved digital holographic reconstruction algorithm for depth error reduction and elimination of out-of-focus particles. *Opt Express* 18, 2426-2448, doi:10.1364/OE.18.002426 (2010).

27 Mullaney, P. F., Van Dilla, M. A., Coulter, J. R. & Dean, P. N. Cell Sizing: A Light Scattering Photometer for Rapid Volume Determination. *Review of Scientific Instruments* 40, 1029-1032, doi:doi:http://dx.doi.org/10.1063/1.1684143 (1969).

28 Mullaney, P., Van Dilla, M., Coulter, J. & Dean, P. Cell sizing: a light scattering photometer for rapid volume determination. *Rev. Sci. Instrum.* 40, 1029-1032 (1969).

29 Choi, W. et al. Tomographic phase microscopy. *Nature methods* 4, 717 (2007).

30 Maltsev, V. P., Hoekstra, A. G. & Yurkin, M. A. Optics of white blood cells: optical models, simulations, and experiments. *Exp Tech* 4 (2011).

31 Liu, P. et al. Cell refractive index for cell biology and disease diagnosis: past, present and future. *Lab on a Chip* 16, 634-644 (2016).

32 Liang, X., Liu, A., Lim, C., Ayi, T. & Yap, P. Determining refractive index of single living cell using an integrated microchip. *Sensors and Actuators A: Physical* 133, 349-354 (2007).

33 Daniels, V. G., Wheater, P. R., & Burkitt, H. G. *Functional histology: A text and colour atlas.* (Edinburgh: Churchill Livingston 1979).

34 X. Liang, A. L., C. Lim, T. Ayi, and P. Yap. Determining refractive index of single living cell using an integrated microchip. *Sensors and Actuators A: Physical* 133, 349-354 (2007).

35 Zhao, Y., Schiro, P. G., Kuo, J. S., Ng, L. & Chiu, D. T. Method for the accurate preparation of cell-spiking standards. *Analytical chemistry* 81, 1285-1290 (2008).

36 Huang, L. R., Cox, E. C., Austin, R. H. & Sturm, J. C. Continuous particle separation through deterministic lateral displacement. *Science* 304, 987-990 (2004).

37 Ozkumur, E. et al. Inertial focusing for tumor antigen-dependent and -independent sorting of rare circulating tumor cells. *Science translational medicine* 5, 179ra147-179ra147 (2013).

38 Hou, H. W. et al. Isolation and retrieval of circulating tumor cells using centrifugal forces. *Scientific Reports* 3, 1259, doi:10.1038/srep01259 http://www.nature.com/articles/srep01259#supplementary-information (2013).

39 Duffy, D. C., McDonald, J. C., Schueller, O. J. & Whitesides, G. M. Rapid prototyping of microfluidic systems in poly (dimethylsiloxane). *Anal. Chem.* 70, 4974-4984 (1998).

What is claimed is:

1. A digital holographic microscope to enumerate cells in bulk flow comprising:
   a laser source for providing a laser beam;
   a micro-objective, a pinhole device and a collimating lens in optical communication with the collimated laser beam;
   a mirror in optical communication with the collimated laser beam;
   a sample chamber in optical communication with the mirror, wherein the sample chamber comprises a sample flow inlet on a first side of the sample chamber connected to a sample flow outlet on a second side of the sample chamber by a microchannel, wherein a sample comprising numerous cells is transported at a bulk flow rate through the microchannel from the sample flow inlet to the sample flow outlet;
   a detector in optical communication with the microchannel, wherein the collimated laser beam passes through microchannel and interacts with the numerous cells to generate a respective hologram at the detector;
   wherein the detector is connected to a processor that calculates a numerical reconstruction from the respective hologram; and
   wherein the processor generates a focused image of the numerous cells using the numerical reconstruction, wherein the numerous cells are enumerated by looking at a size, a maximum intensity and a mean intensity of the focused image.

2. The device of claim 1, wherein the sample chamber comprises more than two parallel paths to accommodate more than two parallel samples.

3. The device of claim 1, further comprising a loading stage having more than two parallel sample paths in parallel communication with more than two parallel paths in parallel communication with more than two parallel microchannels to accommodate more than two parallel samples.

4. The device of claim 1, wherein the processor finger-prints the numerous cells based on wherein the numerous cells are enumerated by looking at the size, the size maximum intensity and the size mean intensity of the focused image.

5. The device of claim 1, wherein the hologram is recorded and transferred to a computer and a three-dimensional numerical reconstruction of the focused image of sample in the 3D volume is generated using the hologram and a z-location of the focused image formed by the profile of a gradient of intensity along a z-direction.

6. The device of claim 1, wherein the detector records an in-focus image of the sample based on a numerical reconstruction from the hologram.

7. A digital holographic microscope comprising:
   a laser source for providing a laser beam;
   a micro-objective, a pinhole device and a collimating lens in optical communication with the collimated laser beam;
   a mirror in optical communication with the collimated laser beam;
   a sample chamber in optical communication with the mirror, wherein the sample chamber comprises a sample flow inlet on a first side of the sample chamber connected to a sample flow outlet on a second side of the sample chamber by a microchannel, wherein a sample is transported at a flow rate through the microchannel from the sample flow inlet to the sample flow outlet; and
   a detector in optical communication with the microchannel, wherein the collimated laser beam passes through microchannel and interacts with the sample to generate a hologram at the detector, wherein numerous cells are enumerated by looking at a size, a maximum intensity and a mean intensity of a focused image.

8. The microscope of claim 7, wherein the sample chamber comprises more than two parallel paths to accommodate more than two parallel samples.

9. The microscope of claim 7, further comprising a loading stage having more than two parallel sample paths in parallel communication with more than two parallel paths in parallel communication with more than two parallel microchannels to accommodate more than two parallel samples.

10. The microscope of claim 7, wherein a processor finger-prints of numerous cells based on wherein the numerous cells are enumerated by looking at the size, the maximum intensity and the mean intensity of the focused image.

11. The microscope of claim 7, wherein the hologram is recorded and transferred to a computer and a three-dimensional numerical reconstruction of the focused image of the sample in the 3D volume is generated using the hologram and a z-location of the focused image formed by the profile of a gradient of intensity along a z-direction.

12. The microscope of claim 7, wherein the detector records an in-focus image of the sample based on a numerical reconstruction from the hologram.

13. A method of quantifying tumor cells using a digital holographic microscope comprising the steps of:
   providing a digital holographic microscope comprising a laser source for providing a laser beam:
      a micro-objective, a pinhole device and a collimating lens in optical communication with the collimated laser beam;
      a mirror in optical communication with the collimated laser beam;
      a sample chamber in optical communication with the mirror, wherein the sample chamber comprises a sample flow inlet on a first side of the sample chamber connected to a sample flow outlet on a second side of the sample chamber by a microchannel, wherein a sample is transported at a flow rate through the microchannel from the sample flow inlet to the sample flow outlet; and
      a detector in optical communication with the microchannel, wherein the collimated laser beam passes through microchannel and interacts with the sample to generate a hologram at the detector;
   passing a sample through the microchannel;
   contacting the sample with the collimated laser beam to form a sample image;
   recording one or more sample characteristics;
   providing a catalog of reference images defining one or more reference characteristics;
   comparing the one or more sample characteristics to the one or more reference characteristics to generate an analyzed sample; and
   using the analyzed sample to quantifying the sample content, wherein numerous cells are enumerated by looking at a size, a maximum intensity and a mean intensity of a focused image.

14. The method of claim 13, wherein the sample chamber comprises more than two parallel paths to accommodate more than two parallel samples.

15. The method of claim 13, further comprising a loading stage having more than two parallel sample paths in parallel communication with more than two parallel paths in parallel communication with more than two parallel microchannels to accommodate more than two parallel samples.

16. The method of claim 13, further comprising fingerprinting the numerous cells based on wherein numerous cells are enumerated by looking at the size, the maximum intensity and the mean intensity of a focused image.

17. The method of claim 13, further comprising recording the hologram is recorded to a computer and a three-dimensional numerical reconstruction of the focused image of sample in the 3D volume is generated using the hologram and a z-location of the focused image formed by the profile of a gradient of intensity along a z-direction.

18. The method of claim 13, further comprising transferring the hologram to a computer and a three-dimensional numerical reconstruction of the focused image of sample in the 3D volume is generated using the hologram and a z-location of the focused image formed by the profile of a gradient of intensity along a z-direction.

19. The method of claim 13, further comprising recording and transferring the hologram to a computer and a three-dimensional numerical reconstruction of the focused image of sample in the 3D volume is generated using the hologram and a z-location of the focused image formed by the profile of a gradient of intensity along a z-direction.

20. The method of claim 13, wherein the detector records the in-focus image of the sample based on a numerical reconstruction from the hologram.

\* \* \* \* \*